United States Patent [19]
Thalhammer-Reyero

[11] Patent Number: 5,930,154
[45] Date of Patent: Jul. 27, 1999

[54] COMPUTER-BASED SYSTEM AND METHODS FOR INFORMATION STORAGE, MODELING AND SIMULATION OF COMPLEX SYSTEMS ORGANIZED IN DISCRETE COMPARTMENTS IN TIME AND SPACE

[75] Inventor: Cristina Thalhammer-Reyero, Framingham, Mass.

[73] Assignee: InterTech Ventures, Ltd., Wellesley, Mass.

[21] Appl. No.: 08/889,624

[22] Filed: Jul. 8, 1997

Related U.S. Application Data

[63] Continuation of application No. 08/373,688, Jan. 17, 1995, abandoned.

[51] Int. Cl.$^6$ .................................................... G06G 7/48
[52] U.S. Cl. .......................................... 364/578; 345/349
[58] Field of Search .................................... 345/326, 339, 345/348, 356, 965, 969, 967, 349; 364/188, 578

[56] References Cited

U.S. PATENT DOCUMENTS

| 5,379,366 | 1/1995 | Noyes ........................................ 395/54 |
| 5,443,791 | 8/1995 | Cathcart et al. ..................... 364/188 X |
| 5,657,255 | 8/1997 | Fink et al. .............................. 364/578 |
| 5,808,918 | 9/1998 | Fink et al. .............................. 364/578 |

FOREIGN PATENT DOCUMENTS

| 0 367 544 | 5/1990 | European Pat. Off. ........ G05B 13/02 |
| WO91/06050 | 5/1991 | WIPO . |

OTHER PUBLICATIONS

Kiezulas, C.J., et al., "Entwicklung von Expertensystemen," XP000268407, *Künstliche Intelligenz, Elektronik*, 40 (22) :122–123, 128–134 (Oct. 1991).

Karp, P.D., et al., "EcoCyc: Encyclopedia of *E. Coli* Genes and Metabolism," http://www.sri.com/ecocyc/ecocyc.htme.

Karp, P.D., et al., "EcoCyc User's Guide, Version 2.4," *Nikos Drakos, Computer Based Learning Unit, University of Leeds* (1993, 1994).

(List continued on next page.)

*Primary Examiner*—Matthew M. Kim
*Assistant Examiner*—Crescelle N. dela Torre

[57] ABSTRACT

The present invention describes an integrated computer-based system, methods, and graphical interfaces, providing an environment for development and deployment of visual models of complex systems organized in discrete time and space compartments, used for graphic information storage and retrieval, visual modeling and dynamic simulation of said complex systems. In the current implementation the system comprises libraries of knowledge-based building-blocks that include sets of icons representing chemical processes, the pools of entities that participate in those processes, and the graphical description of those entities, encapsulating both information and mathematical models within the modular components, in the form of attributes or in the form of component icons, and a plurality of methods are associated with each of the icons. The models are built by linking each pool to one or several processes, and each process to one or several pools, resulting in complex networks of multidimensional pathways. A number of functions and graphical interfaces can be selected from the menus associated with each icon, to extract in various forms the information contained in the models built with those building blocks. Those functions include the creation of interactive networks of pathways, complex predefined queries based on the relative position of pools of entities in the pathways, the role that the pools play in the processes, the location in compartments, and the structural components of the entities of those pools, and dynamic quantitative simulations. The system integrates inferential control with quantitative and semi-quantitative simulation methods, and provides a variety of alternatives to deal with complex dynamic systems and with incomplete and constantly evolving information and data.

48 Claims, 18 Drawing Sheets

OTHER PUBLICATIONS

Karp, P.D., et al., "Guide to the EcoCyc Schema," *Artificial Intelligence Center, SRI International, 333 Ravenswood Ave., Menlo Park, CA 94025, pkarp@ai.sri.com* (Sep. 1995).

Ball, S.S., et al., "Senex: Knowledge Representation in Molecular Pathology," *Department of Pathology, University of Mississippi, Alpers Neuropathology Laboratory, Thomas Jefferson University, Philadelphia, PA* (No date given).

Widman, L.E., "Semi–Quantitative "Close–Enough" Systems Dynamics Models: An alternative to Qualitative Simulation," *Artificial Intelligence Simulation and Modeling*, pp. 159–189 (No date given).

Walther, S., et al., "Object–Oriented Data Management for Distributed Scientific Simulations," *Society for Computer Simulation, Western Multiconference, Proceedings* (Jan. 1993).

Uckun, S., "Model–Based Reasoning in Biomedicine," *Critical Reviews in Biomedical Engineering* 19 (4) :261–292 (1992).

Kocabas, S., "Computational Models of Scientific Discovery," *The Knowledge Engineering Review*, 6 (4) :259–305 (No date given).

Coppella, S.J., "A Mathematical Description of Recombinant Yeast," *Biotechnology and Bioengineering*, vol. 35:356–374 (1990).

Karp, P.D., et al., "Representations of Metabolic Knowledge: Pathways," *Proceedings Second International Conference on Intelligent Systems for Molecular Biology, Menlo Park, CA, AAAI Press* (1994).

Karp, P.D., et al., "Automated Drawing of Metabolic Pathways," *Proceedings of the Third International Conference on Bioinformatics and Genome Research*, H. Lim, C. Cantor and R. Bobbins eds. (Sep. 1994).

Karp, P.D., et al., "Representing, Analyzing, and Synthesizing Biochemical Pathways," *IEEE Expert*, pp. 1–27 (May 1994).

Reddy, V.N., et al., "Qualitative Analysis of Biochemical Reaction Systems," *Dept. of Chemical Engineering, Northwestern University, Evanston, IL*, pp. 1–9 (No date given).

Reddy, V.N., et al., "Petri Net Representations in Metabolic Pathways," *Proceedings ISMB–93, AAAI Press*, pps. 1–9 (1993).

Kazic, T., "Reasoning About Biochemical Compounds and Processes," *Second International Conference on Bioinformatics, Supercomputing and the Human Genome Conference, Proceedings*, pp. 1–17 (1993).

Ball, S.S., et al., "Senex: Symbolic Representation in Molecular Pathology," *Department of Pathology, University of Mississippi, Jackson, MS, and Department of Neurology, Thomas Jefferson University, Philadelphia, PA* (No date given).

FIGURE 2

COMPUTER-BASED SYSTEM AND METHODS FOR INFORMATION STORAGE, MODELING AND SIMULATION OF COMPLEX SYSTEMS ORGANIZED IN DISCRETE COMPARTMENTS IN TIME AND SPACE

This application is a continuation of application Ser. No. 08/373,688, filed Jan. 17, 1995, now abandoned.

REFERENCES CITED

A. PUBLICATIONS

1. L. E. Widman, (1991) "Semi-Quantitative 'Close-Enough' Systems Dynamics Models: An Alternative to Qualitative Simulation", in Artificial Intelligence, Simulation and Modeling, L. E. Widman and K. A. Laparo, eds, Wiley, N.Y.
2. Coleman, T. G. and Hall J. E. (1992) A mathematical model of renal hemodynamics and excretory function. In "Structuring Biological Systems. A computer Modeling Approach" pp. 89–124, Ed. S. S. Iyengar, CRC Press, Boca Raton, Fla.
3. Zygourakis, K., Markenscoff, P. and Bizios, R. (1991) Proliferation of anchorage-dependent contact-inhibited cells. I. Development of theoretical models based on cellular automata. Biotechnology and Engineering Vol.38, pp 459–470.
4. Kromenaker S. J. and Srienc F. (1991) Cell-cycle-dependent protein accumulation by producer and non-producer murine hybridoma cell lines: A population analysis. Biotechnology and Engineering Vol.38, pp 459–470.

Notes

1. The body of the present application has sections that may contain some discussion of prior art teachings, intermingled with discussion of innovative and specific discussion of the best mode to use that prior art in this invention as presently contemplated. To describe the preferred embodiments, it is necessary to include in the discussion the capabilities offered by the shell used as development and deployment framework for this invention (hereafter referred to as "the Shell"). The applicant specifically notes that statements made in any of those sections do not necessarily delimit the various inventions claimed in the present application, but rather are included to facilitate the process to explaining how the workings of an existing set of tools is used to illustrate the preferred embodiments of the new tools and applications claimed in the Claims section. The currently preferred embodiment of this invention, as described in the present application, is based on the definitions of a particular Shell: Gensym Corp.'s G2 Expert System. There are several other attributes that relate to the Shell's built-in performance and formatting capabilities, which are not shown in those examples. Some information included within the body of this application was extracted from various sources describing the characteristics of G2, including user manuals, and some of this material is subject to copyright protection.

BACKGROUND OF THE INVENTION

A. Field of the Invention

1. The present invention relates to a computer-based system, methods and graphical interface which integrates capabilities for graphical information and data storage, modeling, and simulation of complex systems, and which modularizes the information and data in a hierarchy of organized sets of composite icons comprising: phase icons, representing discrete time compartments and location icons, representing discrete space compartments, which in turn contain sets of reservoir icons, representing pools of entities, process icons, representing processes where the entities participate, and entity icons, representing the description of the entities. In addition, the phase icons, reservoir icons, and process icons comprise a set of quantitative variables and parameters, and a set of associated methods that permit real-time simulations of the graphic models created with those modular components. The graphical interface further provides quick access to several automated methods for compiling, retrieving, and displaying the modular components of the graphic models and their contained information and data.

B. Related Applications

1. This application is related to the patent entitled "Computer-Based System, Methods and Graphical Interface for Information Storage, Modeling and Simulation of Complex Systems" invented by the same inventor and filed with this application in the United States Patent and Trademark Office with Ser. No. 08/373,992. This application is incorporated here by this reference.

C. Brief Description of a Modeling and Simulation System for Chemical Pathways 1. The computer-based system object of this invention is implemented as an application developed on top of the computer-based system object of the accompanying patent filing with Ser. No. 08/373,992. Therefore, the system, methods and graphical interface object of this invention are an extension of the system, methods and graphical interface described in detail in the accompanying patent filing, which are here included by reference, and which will not be here repeated unless modifications are introduced. In some cases, alternative implementations are included. The object of the accompanying filing is a system for graphical information and data storage, modeling, and simulation of complex systems, and more in particular of complex systems in the chemical domain, with the implementation focusing on modeling of the mechanisms and the overall architecture of chemical and biochemical pathways, and the simulation of the kinetics of those pathways. The current invention adds two levels of complexity to such system by adding the dimensions of time and space, allowing to model even more complex systems. The current embodiment of this invention graphically models higher levels of complexity represented by complex cellular systems, and it is based on the system, methods and graphical interface already described, and on additional innovative systems, methods and graphical interfaces which are innovative teachings of the present invention. The reader is advised to read said accompanying patent filing for the details of the system already described, which in conjunction with the present filing provides a complete description of the system, methods and interface of this invention. Here we will mainly refer to those new aspects that refer to the higher complexity, and to additional searching capabilities that have been added to take advantage of the knowledge contained in the architecture of the system.

2. This system integrates a variety of forms of knowledge representation, some of them totally novel, while some of these forms may have been given a previous treatment by other authors which may be similar in some of its aspects to the treatment given in the current embodiment of this invention. However, upon integration into a totally new approach, that treatment becomes a part of a novel representation and innovative system. For example, regarding the semi-quantitative simulation component, which is just one of several applications offered by the system object of this invention, L. E. Widman (1991) describes a semi-quantitative simulation of dynamic systems in a totally different domain. What both systems have in common is the assumption that, as stated by Widman: "a semi-quantitative model . . . is intended to predict correctly the direction in which each variable will change and to provide a correct partial ordering of the magnitude of change relative to other variables in the model. . . . The questions can be answered in terms of relative quantities rather than absolute quantities. . . . model parameters that are not specified explicitly are given the implicit, default values of 'normal' (unity) . . . ". Similar but different concepts are applied in developing part of the system of this invention, but as it will become clear from the detail descriptions in the following sections, not only are they applied to a new domain, but the innovative tools and methods used in the present implementation are also quite different. For example, while he assumes that ". . . the default, or implicit, value of 'normal' maps onto unity for parameters and onto zero for variables . . . " the assumption in the prebuilt modular components in the current implementation differs from that statement in that the default, or implicit, value of 'normal' may map onto values other than unity for parameters and onto values other than zero for variables, with those values being defined based on expert knowledge.

SUMMARY OF THE INVENTION

A. An important teaching of this invention is the method of representing the vast breath of knowledge implicated in complex systems in general, and in biological systems in particular. The current embodiment of this invention uses object-oriented design techniques for declaratively representing composition, behavior and interactive information. As is the case for the system described in the accompanying patent filing with Ser. No. 08/373,992, the system of this invention provides several classes of development tools and methods that are hidden from the end-user, including the group of inference and simulation structures. The end-user can create new objects by instantiating existing classes of simple objects, or by cloning and editing existing instances of composite objects with predefined components in their subworkspaces, but cannot define new classes of objects. The system of this invention allows the expert to encode the knowledge about complex systems in a set of compartmentalized modules that describe the composition, architecture and parameters of the system to be modeled, without the need of traditional programming. The application used to illustrate the current implementation of this invention is the functional modeling and dynamic simulation of the molecular mechanisms involved in intercellular and intracellular signaling pathways, which interact with each other to form a multidimensional network of pathways with a large number of components each. The presently preferred embodiments describe examples based on experimental data or models obtained from published materials, selected for the purpose of covering different aspects of modeling biological behavior that may present particular challenges. This is an example of the many potential applications of the system of this invention, however, and it should not be construed to limit the applicability of this system to the numerous other applications that involve complex systems in any other domain, which can be developed by minor modifications or additions of the system using the methodology here presented.

B. Of major importance in simulating the behavior of complex systems is the need to model the different quantities and states at which the entities can be found in particular locations at different points in time, and also to model the events that cause the transitions from one state to another, or the translocation from one location to another, or the progress to the next phase in the time sequence. Some of the important teachings of this invention comprise: the representation of those states, transitions, and locations; the methods to implement their graphic modeling; and the methods to dynamically simulate the dynamics of the pools of entities in each state, location, or phase. In the particular domain implemented to illustrate this invention, there are several major types of states and transitions to be considered, depending of whether the entity to be considered is a biological system, organ, cell, cellular compartment, molecule or any other of their components. We are providing here with just a few examples considered in the currently preferred embodiment of this invention.

C. The system in the current implementation of this invention is, like the one in the accompanying filing with Ser. No. 08/373,992, composed of modular complex functional tools or "bioObjects", which are objects represented by icons. A new hierarchy of subclasses of bioModel have been defined for this application, with subclasses representing different types of phases or other time intervals, and location compartments representing different types of locations . These bioModels, and the methods attached to them, encode knowledge that enables the program to reason about the containment of different parts of the model in several compartments, while the architecture of the network of connected bioObjects of diverse types is transparently maintained, regardless of the transfer of the bioObject icons to different locations. They also comprise quantitative variables and parameters, some relating to quantities and rates of conversion of rates of translocation, distributed as before within the corresponding reservoirs and process and others relating to time intervals which may also be associated with the phase compartments, all of which have associated simulation formulas to compute their values. Those variables allows to dynamically simulate the modular quantitative model encapsulated in those bioObjects, based on the environmental and initial conditions selected by the user. In addition, the modeler can define expert rules to monitor the values of those variables while the simulation is running, and to either set other values or control the course of the simulation in a variety of ways. The expert rules can also reason about time or about events resulting from the simulation. Inference using those types of knowledge may direct further actions to be executed by the system.

D. The bioModels here described can be viewed as composed of two major types of knowledge structures:

1. The system's architecture is defined by the connected subcomponents of the system that are relevant to its function. Each subcomponent is defined using experimentally obtained qualitative information, such as the identification of the biological entities and processes involved, the knowledge about their localization within discrete physiological compartments in space and time, and about the relationships and qualitative interactions between those entities. This information is mapped into the graphic knowledge structures represented by the different classes of schematic tools. This representation allows visualization of mental scientific models, and can in addition be used to track what influenced the simulated response. Reasoning about this architecture is used within the navigation and query capabilities provided by CABE.

2. The modeled system's behavior is defined by mathematical components, represented by a set of model differential and algebraic equations that provide the values of the system's variables and describe their behavior, together with the set of associated parameters that control the behavior of the variables and the system as a whole. The system's variables and parameters are embedded and distributed throughout the system of connected structures, encapsulated within the subcomponents that define the system's architecture. The model can then be viewed as a set of embedded block diagram representations of the underlaying equations that can be used for dynamic numerical simulation and prediction of the effects of perturbations on the system, and to ask what-if type questions.

E. Like the previous system, this invention and its various embodiments describe systems and methods that combine inference rules with qualitative and quantitative modeling tools, to model complex systems. Further important teachings of this invention comprise: a) the representation and storage of information and data about networks of interacting entities, together with information about the physical description of those entities, the processes in which they participate, the location where the interactions take place, as well as the sequence in time of the interactions, if applicable, in a modular and usable knowledge form; b) the methods to store the available information and data about those complex models into modular, modifiable, expandable and reusable knowledge structures; c) the representation and storage of information and data about of the complex systems in graphic models that make use of several layers of encapsulation, which allows to hide the details in several layers and allows the user to display only the level of detail desired; d) the methods to perform queries that in addition to combine criteria related to the structural composition of the bioEntities involved, the position of bioPools downstream or upstream of the bioPool taken as reference, the role that those pool of entities play in processes, or any combination of the previous three, now can add, in combination with the previous, new search criteria related to the location of those pools and processes in the location and phase compartments; and e) the methods to dynamically simulate their continuous interactions, modifications and translocations to other compartments, and the time-dependency of such interactions, such as the compartmentalization of processes within the life cycle of a larger encompassing entity.

F. Because of the complex interrelationships driving the processes in molecular cell biology, it is an objective of this invention to create an environment to allow domain-experts to directly enter that knowledge, and to create and modify models as needed based on experimentation, without the need of knowledge engineers as intermediaries. The innovations of this invention include but are not limited to the specific design, building, and use of those objects to allow interpretation, representation, modeling and simulation of entities and their states, relations, interactions, the pool of those entities and the processes in which they participate, their discrete compartmentalization in time and space, as well as the concepts that make the simulation of this very complex systems possible. The overall domain knowledge-base can be built as a set of topical-modules, focusing each on different subsystems. Each of the topical-modules can be run on top of the repository module, and they can be dependent or independently of each other, or they can be maintained in separate CPUs and seamless integrated by the Shell's supervisor. In addition, those functional objects, together with the required specific interfaces, permit domain-expert users to build their own situation-specific applications. The domain knowledge can be quickly built into the system by using the paradigm of "Clone, Transfer, and Configure", creating new bioObjects by cloning and editing the generic bioObjects that form the knowledge library or repository that can be constructed using the methods of this invention. User configuration of the bioObjects in this system consists primarily of connecting graphical objects and filling out tables, and the building of bioModels requires no programming other than the use of this graphical language.

G. The system of this invention is an application built on top of the system described in an accompanying patent filing with Ser. No. 373,992, and can be considered as an extension to the system described in said filing where the definition of additional classes of objects and their related methods is required. Such additional tools and methods allow modeling of two new dimensions of complex systems, those of space and time constrains. Among those new tools is a library of complex structures, called bioModels in the current implementation, used to combine specific sets of pathways, which are further compartmentalized in location and in time.

H. Specifically, major teachings of this invention are tools and methods used to:

1. represent the qualitative and quantitative description of the participating components and the dynamics of molecular and cellular interactions, using an object-oriented methodology that spans the analysis, design and programming phases;
2. construct composite complex models, comprising any number of other complex models that integrate biochemical pathways;
3. store qualitative and quantitative data and knowledge, including the compartmentalization of those models within discrete physiological spaces and time intervals;
4. use the composite models to dynamically simulate intracellular and intercellular pathways, cross-talk between the pathways, their combinatorial regulation, and forward and feedback loops, under physiological, pathological, pharmacological or toxicological conditions.

I. Taking into consideration the fact that when dealing with complex systems, some parts of the system may be more precisely defined than others, the system of this invention integrates a variety of methods to allow modeling and simulations while accommodating the uneven types of knowledge available. The following describes how the heterogeneous forms of knowledge are integrated in the system of this invention:

1. In some cases, sufficient information has allowed scientists to develop mathematical models to represent a particular behavior of a system, and some of those models may be suitable for adaptation to be included in the knowledge-base, giving the user the option to integrate them in their simulations. This type of knowledge is usually included in the form of the parameters characteristic of the system, or the initial conditions, once the underlaying architecture of the network is matched.
2. Intermediate levels of information about a sequence of events, or effects following a cause or combination of causes, allows the construction of semi-quantitative behavioral nets that are constrained by the data available, such as time intervals, context and compartments in which behaviors occurred, concentration levels at which different behaviors were observed, and so on. . . . This type of information is used to design the compartmentalized architecture of the network, and to provide semi-quantitative values to the scaled parameters and initial conditions.

3. Heuristic and shallow knowledge can be integrated in the form of either rules, or formulas for inferred or simulated variables, that connect a cause with a distant effect, without detailed description of the unknown underlaying mechanism.

J. Depending on the amount and type of information and data available about the system to be modeled, and the nature and size of the bioModels to be developed, the system of this invention's may operate in either quantitative or semi-quantitative simulation mode. With well known metabolic pathways, the simulation may be run in quantitative mode, but since in most biological systems both qualitative and quantitative information is incomplete, it may be difficult to simulate with accuracy such biological systems. However, the semi-quantitative methods integrated in the system of this invention allows to gain insight about the degree and direction of change in the model variables, and their quantity levels at different points in time. The system of this invention is to be used by scientists as a new form of interactive research tool to integrate information and data into knowledge structures which characteristics and behavior can be modified and its parameters adjusted as new information and data pertinent to the system under study becomes available.

K. Of major importance in simulating the behavior of biological systems is the need to model the different states in which complex biological entities, such as cells, can be found at different points in time, and also to model the events that cause the transitions from one state to another. There are several major types of states and transitions to be considered, depending of whether the biological entity to be considered is a biological system, organ, cell, cellular compartment, molecule or any other entity. We are providing here with just a few examples among the many considered in the currently preferred embodiment of this invention.

L. The system object of this invention can be used as an interactive research tool that allows users to integrate their experimental data with the knowledge derived from the work of thousands of other investigators that can be incorporated into this system. Encoding and integration of large amounts of information and data can be accomplished in a very efficient manner, based on the inheritance, encapsulation, and clone-and-modify capabilities of the system. Variations in multiple experimental parameters can be rapidly analyzed, and the experimental conditions that produce results of interest in silico can then be tested either in vitro or in vivo. If the results coincide, they validate the model, and if they differ, the investigator can modify either the parameters or the model hypothesis to meet the experimental data. By iterating this process, a level of confidence on the models is built and new hypothesis can be tested. Of particular interest is the modeling and simulation of disease specific conditions, and then testing the effects -both desired and unwanted side effects- of potential therapeutic agents. This system of this invention also allows to analyze disturbances such as potential environmental or biological inducers of disease in both physiological and pathophysiological models. The methods included in this invention can in a similar way be used in a variety of applications, including but not limited to: simulation and prediction of experimental results; interactive drug design; study of drug side-effects and multiple drug interactions; simulation of interactive causes in the induction and progression of disease, including both biological and environmental factors; diagnostics and clinical decision support; therapy planning; theoretical research; and numerous other applications.

BRIEF DESCRIPTION OF DRAWINGS

FIG. 2 is an schematic representation of the organization of domain-specific processes in discrete space compartments and time compartments.

DETAILED DESCRIPTION OF THE CURRENTLY PREFERRED EMBODIMENTS

A. INTRODUCTION

1. This section will discuss various of the innovative teachings of this invention which refer to a system, methods and tools used to store information and data, encapsulated in graphic and interactive models of complex molecular mechanisms and pathways, that allows to:

interactively navigate through those pathways;

perform queries that refer to: a) the structural composition of the bioEntities involved, b) the position of bioPools downstream or upstream of the bioPool taken as reference, c) to the location in cellular compartments of the processes in which those bioPools of bioEntities participate, d) any combination of the previous three; and dynamically simulate the kinetic interactions between the bioPools of bioEntities as schematically defined through the network of connected icons representing appropriate biochemical concepts, to mimic the regulation and function of cellular systems, and which are the subjects of molecular and cell biology.

2. The object-interaction models are inherent in the current embodiment in the way that bioObjects interact with each other through their variables, which dependencies on each other are defined through the schematics. What is new in this invention are the specific encapsulated representations of various forms of interactions and the methods to encode the qualitative and quantitative knowledge about those interactions, while at the same time maintaining a graphic representation that is intuitive for scientists. The object-interactions models comprise: a) methods related to the architecture of the schematic bioObjects and their specific connections, which establish the nature of the specific interactions between them; b) methods that relate the various numeric and symbolic variables and parameters of the connected knowledge structures; e) methods to pass control and data values between the appropriate bioObjects; c) methods that constrain all those interactions in time and location compartments; and f) methods that integrate data and information of different knowledge structures dispersed throughout several workspaces in the knowledge-base.

3. The examples provided to document the current implementation of this invention will focus on modeling biochemical regulatory processes that are relevant for intracellular or intercellular signaling.

Figure 1:
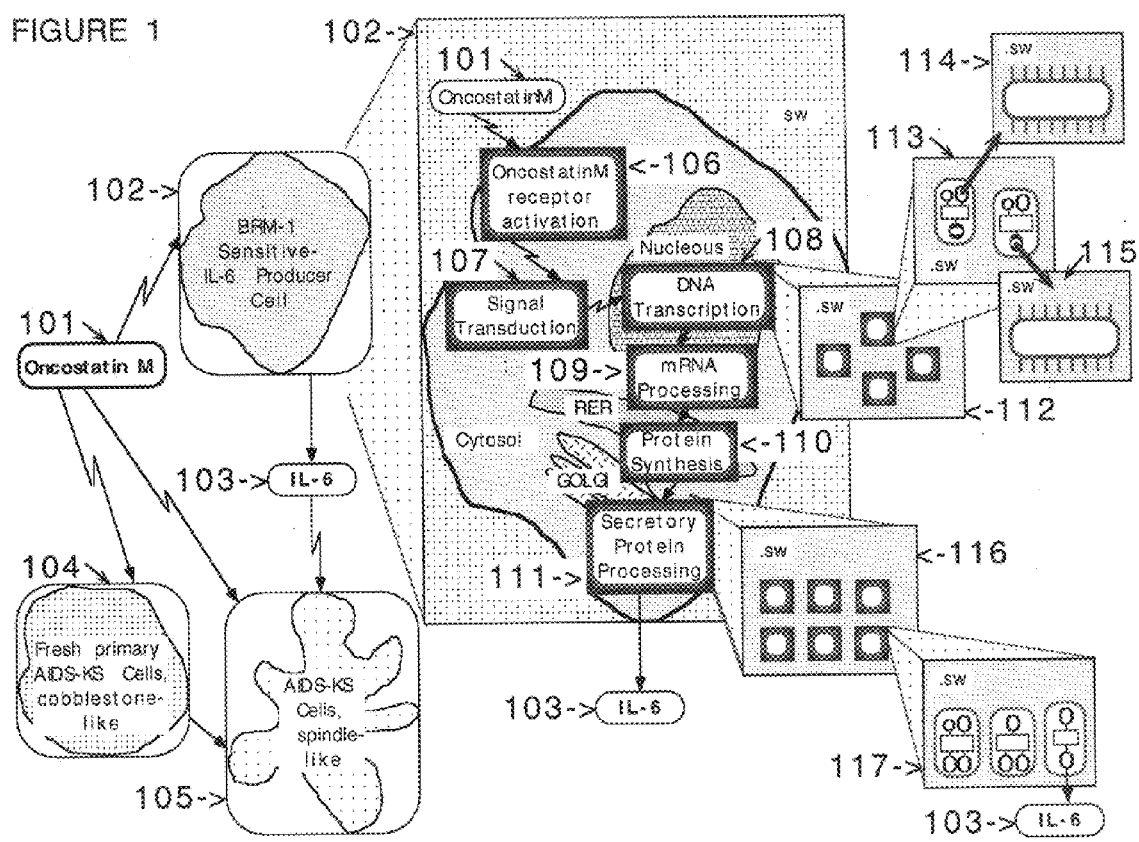
FIG. 1 is an schematic representation of the organization in the system of this invention of the components of the iconic compartmentalized models in the domain of cell biology.

4. The object of this invention is a domain-specific knowledge-based Information and Modeling System capable of being used as a shell by modelers of biological systems to graphically construct graphic and object-oriented databases, which can then be used by the end-user in a variety of modes. Those modes includes the capabilities of querying, navigation and simulation of cellular systems, and have several applications in the biological and biomedical domains. This development and deployment environment is comprised of a set of knowledge-bases including a plurality of tools and methods arranged in hierarchies of classes and workspaces, hereinafter called libraries. This system also provides a library of prebuilt generic bioObjects, classified in palettes that can be selected through provided menus, that a molecular or cell biologist can clone, transfer and modify, to build complex graphic cellular models in the form of a set of nested schematics. As shown in FIG. 1, the currently preferred embodiment is built as a multi-compartment extension of the system described in the accompanying patent application entitled with Ser. No. 08/373,992, developed to model and simulate chemical and biochemical pathways in a one compartment mode. Both systems are developed and deployed on top of a commercially available, real-time development and deployment Shell 5. Among the major teachings of this invention are a plurality of tools and methods that allow the development of graphic models and dynamic simulations of very complex biological systems by the very experts that are able to understand that complex knowledge, but who do not have programing expertise or even an interest in the computer sciences. The system of this invention is an interpretative, and time-driven, event-driven or goal-driven real-time environment that allows rapid building of graphic models that can be easily browsed and understood by the expert end-user. This system defines new classes of bioObjects that are used in cellular models, such as several subclasses of previously defined major classes. One major new class is bioModel, with its various subclasses. This system's graphic interface provides menus pointing to a set of palettes that contain, additional generic bioObjects and a new palette of bioModels that the domain expert can use in conjunction with the bioObjects defined in the previous system. This graphic environment enables reasoning about the interactions between objects and their compartmentalization, and is particularly important because it approaches the format that scientists use to summarize their knowledge and to convey it to others as graphic models, supporting rapid and incremental development, testing, modification and expansion. The accuracy and validity of knowledge-based systems correlates not only with the quality of the knowledge available to the modelers but also with their ability to understand, interpret and represent that knowledge. Because of the complex interrelationships driving the processes in molecular and cellular biology, it is an important objective of this invention to create an environment to allow the domain experts to directly enter that knowledge, and to create and modify models as needed based on experimentation, without the need of knowledge engineers as intermediaries.

6. The wide range of knowledge forms involved in the dynamic simulation of biological mechanisms needs a variety of techniques to simultaneously represent knowledge about, among others: a) the high complexity of cells and organisms, and their activation and differentiation; e) the quantities of each entity in each state in each particular physiological or cellular compartment; f) the succession of states of an entity and their quantities over time; g) the highly regulated interactions between specific states of those entities, and the resulting forward and feedback loops and cross-talk between pathways. To accomplish all those representation goals, innovative methods and tools have been developed which combine the concepts of a variety of model-driven and object-oriented system analysis, which have been integrated into the structure of this system and implemented using the capabilities provided by the selected development Shell. This combination has resulted in a unique approach that satisfy the complex representational needs. The object-oriented system subject of the present invention provides a powerful knowledge representation of biological entities (such as organs, cells, DNA, enzymes, receptors and mediators) and conceptual entities (such as processes and cellular interactions, rates and densities). In the system of this invention, data and behavior are unified in the knowledge structures. The schematic tools used as building blocks to construct the desired models are defined by a combination of two main methods:

In the first method, each of those tools is an object or instance of a class and, like in other object-oriented systems, it is here defined following a class hierarchy. A template is used to define the attributes characteristic of all objects of that class and distinct from other types of objects. Manipulation of the data is performed by operations and methods attached to an object or its superior classes.

The second method is used to graphically define the components of each composite object. This is achieved by encapsulating an schematic of the components within a subworkspace associated with that particular object, connected among them and with others in the knowledge-base in a specific way that define the networked structure of the system. Each of those connected objects may in turn encapsulate a subworkspace with additional objects of a variety of types. Examples of these additional objects, among others utilized in the current implementation of this invention, are model-blocks, inference blocks or tabular functions, that establish the relationships between the variables or parameters defined for that object with the variables or parameters defined for other objects and so on. Since the subworkspace is not inherited through the class hierarchy, neither are the components. The components on a subworkspace can be cloned and transferred onto another subworkspace. However, it is more convenient, once a representative or generic instance for a class is completed with its subworkspace, to clone and transfer the superior object, in which case all encapsulated levels of subworkspaces are also reproduced. This multiple encapsulation within the schematics is a generic mechanism in the system of this invention which allows hiding of unwanted information and the modularity resulting from a multilayered structure with increasing levels of detail. When a bioTool is evaluated, the variables encapsulated within the schematic are used to generate the output values. The combination of these methods allows the biomedical expert to construct reusable libraries of bioModels and simulation modules using only graphic programming.

7. The system of this invention integrates propagation of values, inference and control throughout the pathways. The bioObjects provided in this system are programmed by default for steady-state modeling. A dynamic simulation is initiated after the introduction of desired perturbations or initial conditions by the user. Inputs from the user-interface or from external control systems or databases can be also forward-chained during run-time. A variety of methods are then used to compute or infer new values for the variables or parameters, derive conclusions and pass on control signals, and trigger action sequences, each as appropriate. The required integration of dataflow and sequential control mechanisms is accomplished in the currently preferred embodiment while taking advantage of the intuitive capabilities provided by the graphical architecture, where the bioObjects encapsulate the data to which related methods apply, and the parameters and variables are hidden but their values can be displayed on the schematics. The specific way the bioObjects are connected specify both data flow and control flow, representing sequential or concurrent ordering of procedure execution, and the information needed to execute an algorithm is provided by or inferred from the schematics. For consultative applications of this invention, backward-chaining or procedural routines are used.

8. The principle underlaying this system's dynamic modeling is the network of a combination of state and dependent variables, encapsulated within the structure of the bioObjects contained in the specified bioModel. When simulation starts, the input data initiates a forward chaining which involves both control and data flow from bioReservoirs to its connected downstream bioProcesses, and from these to their connected downstream bioReservoirs, moving along the bioModel's pathways. The bioObjects' evaluation methods execute in sequence during forward chaining, passing along the arguments. The forward and backward associations between bioObjects for runtime execution are either inherent in the connections between the bioObjects or are explicitly configured.

9. Because the applications build with this system can become very large, it is important to have control over which parts of the system are included in a given simulation or navigation. Two achieve this goals two implementations are provided with this system, with each having advantages over the other depending on the hardware facilities available:

In the first implementation, the constraining of the simulation space is achieved by using activatable subworkspaces for complex bioObjects, such as bioReservoirs, bioProcesses, and certain time-compartments, and by having all those structures initialized to a deactivated state. When the subworkspace of an object is deactivated, any structure upon that subworkspace is not seen by the inference engine or the simulator. Only the subworkspaces of the desired structures at any given time are activated, and only their contents are therefore participating in a given simulation and associated inferences. Methods associated with buttons on the entry-panels used for simulations and experiments, activate the subworkspaces of bioObjects connected along the desired pathways and contained within the selected bioModel or compartment, and this activation is necessary for propagating values along the pathways. Inactivation of those subworkspaces occur upon resetting the selection within those panels. This mechanism is also very utile in activating or deactivating entire branches of a simulation model at run-time. The efficiency of large scale simulation applications is further improved by having the initiation of the simulation of different subcomponents of the high-level bioModel be driven by events, when appropriate, or by time intervals. This implementation allows only a single user to run simulations concurrently, since the attribute values of the bioObjects change during the simulation, as well as the activation state of such subworkspaces. For multiple users, multiple processes of the program have to be started.

A second implementation is based in dynamically cloning those bioReservoirs and bioProcesses, or certain time-compartments, required by the simulation, and to use those copies to hold the changing attribute values, rather than the originals. In this implementation, the subworkspaces of bioReservoirs and bioProcesses are not activatable, remaining always activated. On the other hand, the subworkspaces of certain time-compartments are still activatable, are deactivated when created, and their activation is controlled during the simulation, operating as in the first implementation. This implementation allows multiple users to run simulations concurrently, each on a different X-window, but increases the burden on the system by increasing the required RAM to hold the additional transient copies and to run more than one simulation concurrently. Since the system of the current invention is modularized, and the modules can be dynamically up-loaded and down-loaded, part of this problem can be solved by up-loading the module(s) that contain the originals, creating the copies for the various simulations on the top module, and removing the modules that are no longer required from the memory, before the simulation is started.

10. A simulation application can also be distributed among several workstations when the knowledge-base modules are distributed as well and the underlaying Shell is loaded in each of the CPUs, allowing computer resources to be adjusted to achieve the necessary performance. The Shell supports distributed applications with the communications handled transparently by the built-in network protocols. The intelligent graphic user interface supports communication and control activities with messages, charts, readout tables, graphs, meters, dials and controls, which are designed using the output tools provided by the Shell.

B. CELLULAR KNOWLEDGE REPRESENTATION

1. Biological systems are complex, hierarchical, heterogeneous and non-linear systems, which involve an interplay between the processes of transport, reaction and conformational change, regulated by cybernetic flows of information. The principle followed in the current implementation of the system of this invention is based on breaking the knowledge about biological entities, processes and pathways down to small functional units, to a level where the following requirements can be met: a) allowing their repeated use as building blocks in a variety of situations; b) keeping the number of units manageable; and c) allowing access to the structures and processes that are susceptible to biological control and regulation. The currently preferred embodiment of this system uses a kinetic approach to model these biological systems, rather than a thermodynamic interpretation, although thermodynamic variables are also included to allow modification of the behavior of the kinetic system. The current approach, which focus on the quantities of cells and molecules, such as the densities, concentrations or scaled-amounts of each bioReservoir's bioPool, as a continuous function of time, and on specific coefficients or on rate constants that, in conjunction with the current values of those quantities, define the velocity of a bioProcess's bioEngine, and the rates of consumption of certain bioReactants that participate in such bioProcess or the rates of production of its bioProducts, which are dependent on such velocity and specific stoichiometric coefficients, and which are equivalent to the rates at output and input from their connected bioPool, respectively. This kinetic approach is closer to the way of thinking of biochemists and molecular biologists.

2. The cellular representation in the current embodiment of this invention aims to reproduce the fact that function is not inherent in any one component of the cell, but rather emerges from the cooperation of many components, which depend on organization and functional relationships. Live and growth depends upon closed cycles of mutually dependent interactions. In a constant environment, the proportions of the various constituents settle down to constant values and a steady-state is reached. The steady-state correspond to an optimum state, since the lack of such balanced state would lead to rate-limiting steps. When the environment changes, those proportions move towards new values to achieve again optimum growth in the new environment.

Figure 2:
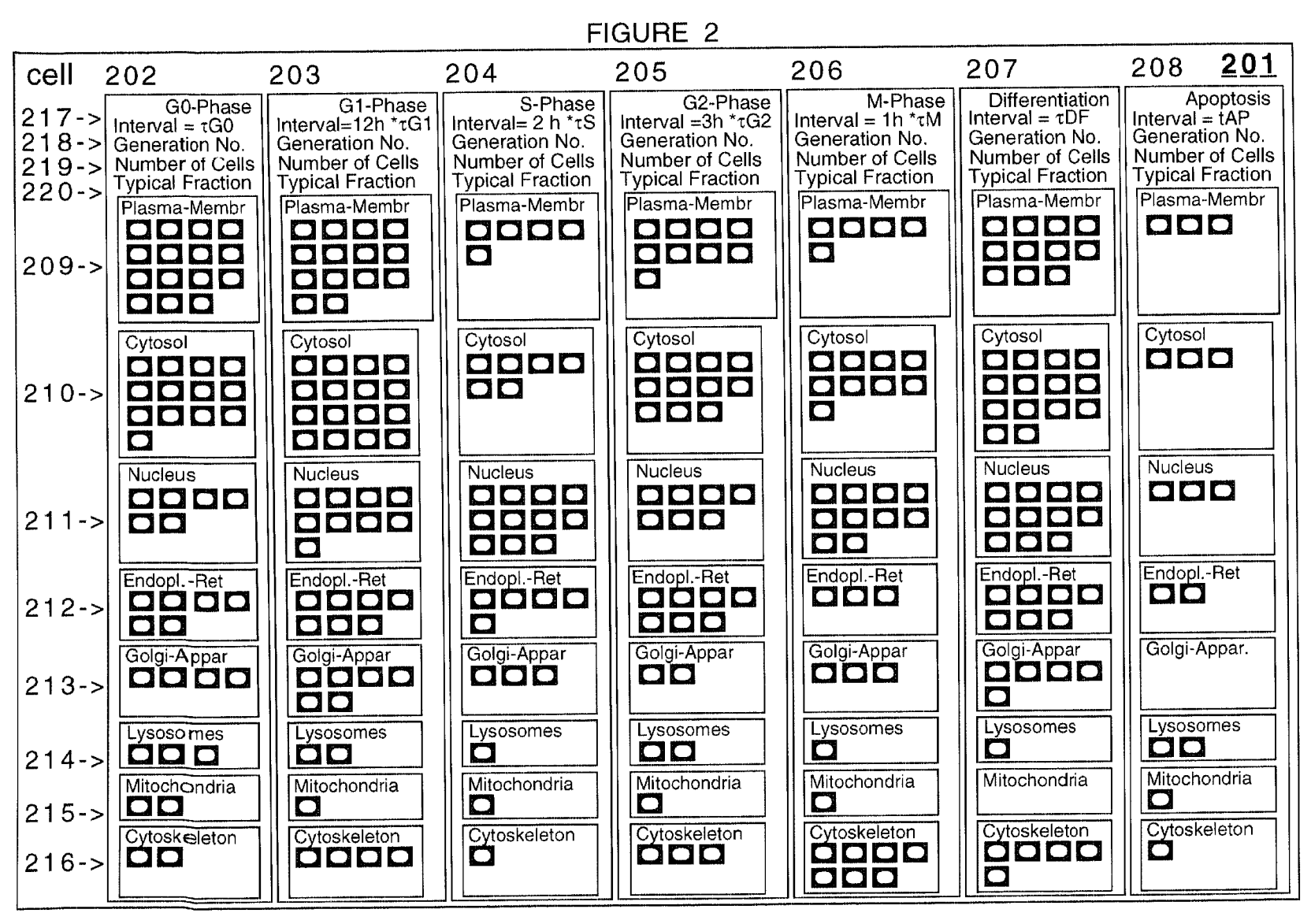
Figure 3:
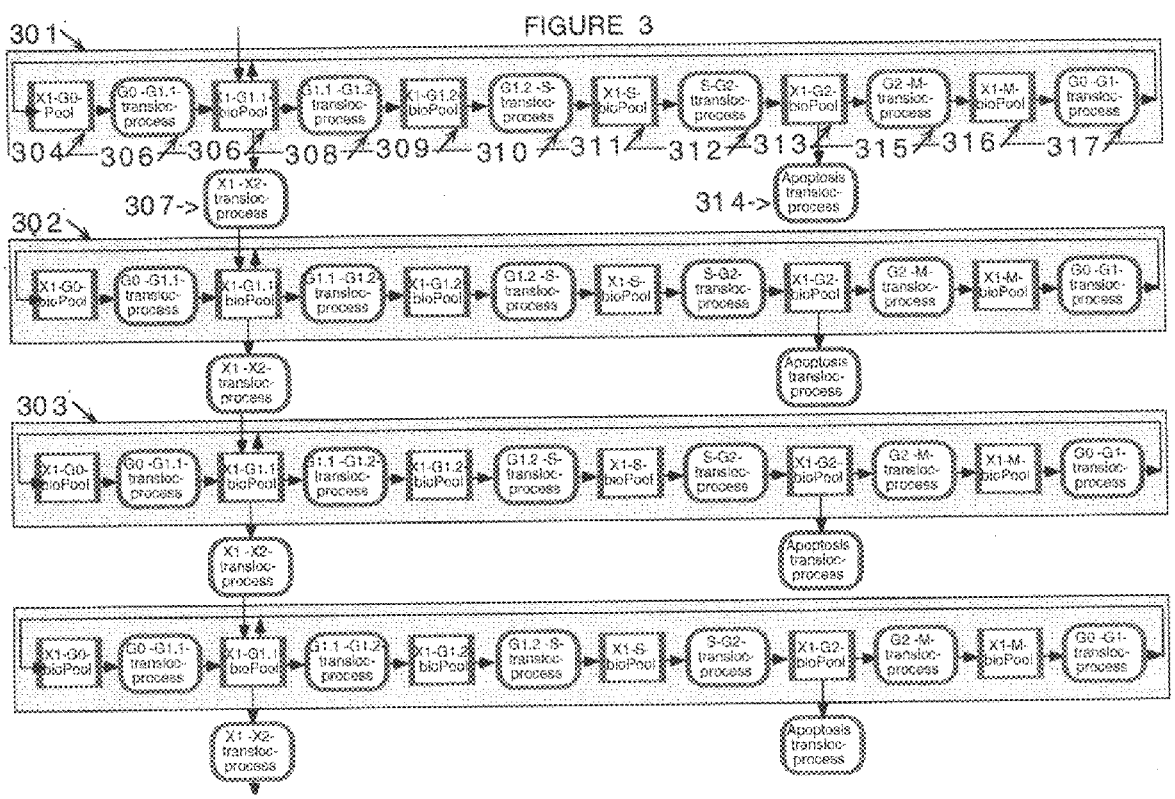
FIG. 3 is an schematic representation of the handling of tne dyniamics of the progression of populations of cells through different states by means of the sets of pools of cells and processes characteristic of this invention.
Figure 12:
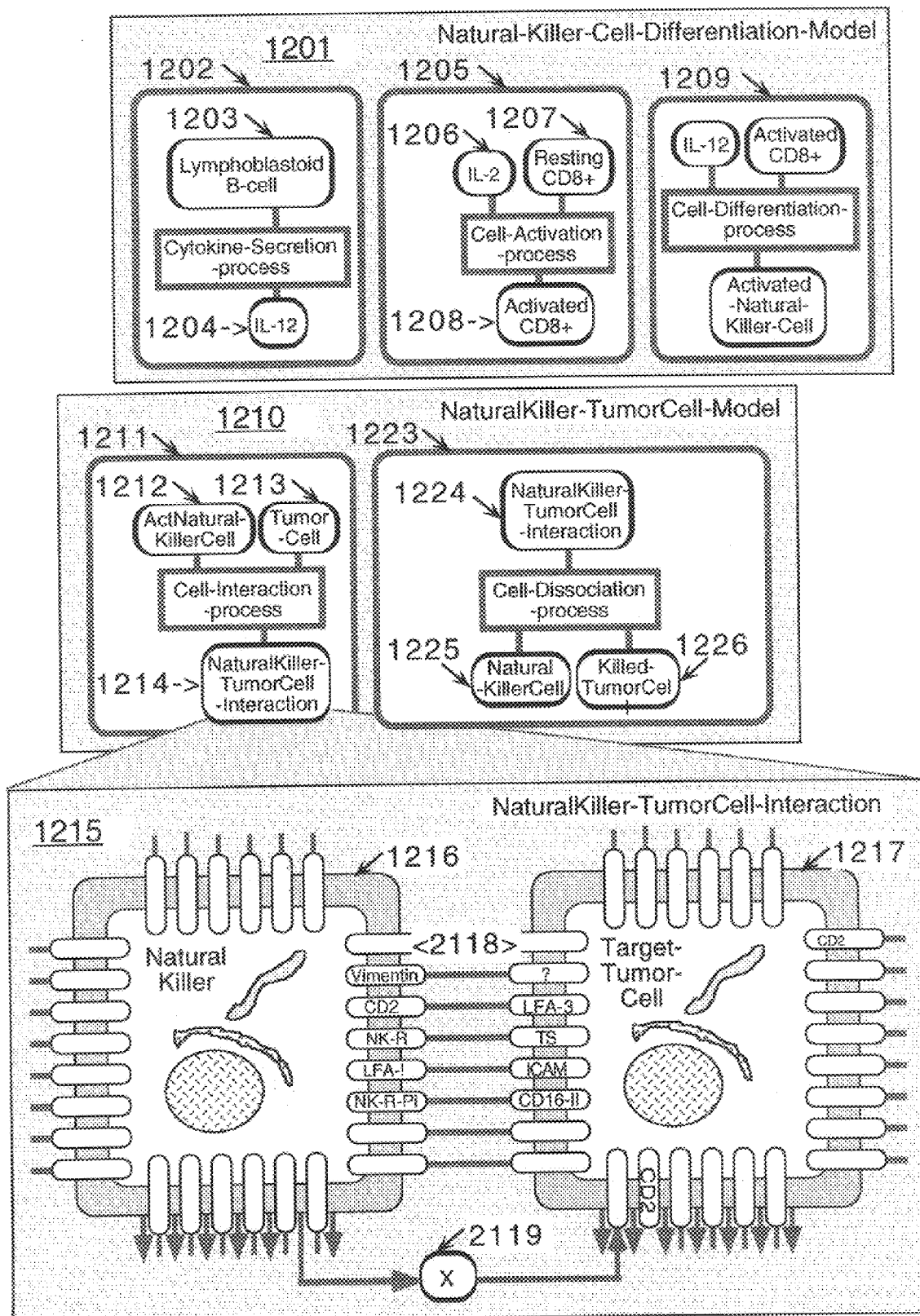
FIG. 12 is a detailed representation focusing on the iconic components of different types of cellular processes.

3. The schematic representation on the left of FIG. 1 shows an abstraction of the types of molecular and cellular relationships and interactions that are modeled and simulated with the system of this invention. This high-level example, at a low-level of detail, can be summarized by what a biomedical expert could describe as "Oncostatin M (101) is a biological response modifier which induces different responses on different cell types: a) it induces certain classes of cells (102) to secrete the cytokine IL-6 (103); b) it induces differentiation of primary, coblestone-like AIDS-KS cells (104) into mature spindle-like AIDS-Ks cells (105), which in turn are capable of long-term growth in agar when c) both Oncostatin M and IL-6 are present". This statement and its graphic representation combine knowledge at very different levels of detail, equivalent to the way human mind can abstract knowledge. For instance, it deals with both molecules and cells as cell-entities as if they were similar types of structures, when in reality that is very far away from the reality. Cells are composed of thousands of different types of molecules. In some cases, the overall pathway within the cell can be known to some extent while in others the mechanism of a biological response may be totally unknown. The system of this invention can be described in very similar terms, on one side, bioPools of cells and molecules can interact with each other, in any combination in a variety of bioProcesses, as shown in FIG. 12 and described in more detail later. On the other hand, the components of the cells can be modeled and analyzed at increasing levels of detail, as contained in various layers of bioModels (102–112), until at the end of the layer hierarchy, the single bioProcesses are represented, and their associated bioReservoirs and bioEntities. FIG. 2 shows how the intermediate submodels are preferentially organized in two types of superior compartments of a cell represented by the different subsequent cell states represented by the cell-phases (202 through 208), and within each of those the cell-compartments (209 through 216) that represent the different cell organelles. While each of the cell-phases contain a detail description of large numbers of components, as encapsulated in the different sublayers, it has in addition a set of characteristic parameters and time-variant attributes (217 through 220) that can be used to model the progression of a population of cells through those compartments. That concept is schematically represented in FIG. 3, where the cells of that population may keep cycling through those phases, if some required conditions are met, as represented hero by the translocation-engines, or they can exit the cycle and differentiate to 302 or dye in 314.

4. The system of this invention deals with multiple levels of biological structural complexity, such as physiological systems, organs and their compartments, cells, subcellular organelles, and molecules. Therefore encapsulation is an important feature exploited by this system. Since unlimited levels of encapsulation are allowed, it is possible to start dealing with a topic with a high-level representation, and then successively "clicking" into objects of interest, to show the next level of detail. In general, the cellular signaling pathways represent repeated cycles, from cell to cell, or some times activating the producer cell as well, such as agonist→receptor activation→signal transduction→gene expression→transcription→translation→post-transcriptional modification→secretion→transportation→(receptor activation). This concept is shown in an abstracted form in FIG. 1 By clicking again and again on objects at each level, one can focus on specific areas at the desired level of complexity. In the one example shown in FIG. 1, this multiple encapsulation process has been abstracted. It illustrates a cell-bioProcess in which, after a cell (102) has been activated by Oncostatin M (101), the secretion of interleukin IL-6 (103) is induced, but only after the sequential activation of numerous biological processes (bioProcesses), involving numerous pools (bioPools) of biological entities (bioEntities), contained in bioReservoirs, which are encapsulated in this simplistic example within higher-level bioModels, such as receptor-activation (106), signal-transduction (107), DNA-transcription (108), mRNA-processing (109), protein-synthesis (110) and secretory-protein-processing (111). Clicking on any of these bioModels displays their subworkspace which may in turn contain a set of other bioModels, such as in (112), and the process can be repeated again as in (113), until reaching bioModels composed only of sets of bioProcesses. The bioPools have been devised to represent the reality of biological systems, which require to refer to populations of cells or molecules with similar properties within a given compartment, rather than to the single biological entities.

5. A cell-bioModel is represented in the system of this invention as a set of bioReservoirs and bioProcesses, systematically organized in the subworkspaces of other bioModels contained in such cell-bioModel, which represent each a separate compartment in time and location, and within those, sets of biologically related processes or pathways. At a higher levels of organization, bioProcesses connected to bioReservoirs of cells or cell-interactions, are organized into bioModels the represent organ compartments, which in turn are organized into organs, and which in turn are organized into into physiological systems. Different cell-bioReservoirs contain either populations of different cell subsets or populations of the same cell subset in different locations. Each of those cell-bioReservoirs makes reference to a predefined cell-bioEntity, which has a characteristic phenotype representative of the cells contained in that cell-bioReservoir. The different phenotypes may characterize: a) different cell lineages, b) different stages of differentiation within the same cell lineage, or c) cyclical changes in the cell characteristics over time, within the same differentiation stage. Phenotypes are sets of characteristics measurable on intact cells, and the transition of cells from one phenotype to another are represented in the present embodiment of this invention as a translocation of a fraction of the cells from the cell-pool of the former subset to the cell-Pool of the later subset. The events that trigger those transitions may be unknown, but they may be recognized by changes in measurable or functional markers, such as the appearance of a new receptor, the synthesis of DNA, the secretion of specific interleukins, or mitosis, and the relative time in which they appear or disappear may be known, in which case those transitions are time-driven. More specifically, a cell-bioEntity, which is a high-level external representation or description of a cell, may make reference to a cell-bioModel, which as described above is internally characterized by its components and mechanisms, represented by the pathways of bioReservoirs and bioProcesses.

6. As in the accompanying patent application, the system of this invention takes advantage of the inheritance capability characteristic of object-oriented environments, and systematically assigns all bioObjects to a hierarchy of classes. At each level of the hierarchy, information common for all the inferior classes branching out of a class (called superior class) is encoded just once, allowing a rapid encoding of generic biological information. Broad classes of objects are defined, using the object-definition templates from the Shell library, to describe large families of biological entities. Within those classes, more closely related entities are further defined in successive inferior classes, until no more distinction between classes is necessary. As described in more detail below, FIGS. 7, 14, 17, 19, and 37 are examples of the hierarchies of the most important classes of bioObject.

7. It is a characteristic of this invention the use of different bioPools to represent populations of a given type of cell or molecule in different states or conformations, and for each location of such populations in particular biological compartments. The fast and short-term regulation, such as the temporary inhibition or activation of enzymatic activity is modeled through separate bioPools of the more active and less active (or inactive) forms. Each modification of molecules or complexes that results in qualitative or relevant quantitative changes in their activity or function, is represented as transfer of units between those different bioPools. Examples of those modifications include post-translational modifications of proteins, including allosteric changes, such as phosphorylation, isoprenylation, and so on.

8. The slower, long-term, regulation of enzymatic activity is modeled by induction or depression of protein synthesis, which optimizes its concentration for the newly required function. Constitutive enzymes and receptors are considered to be synthesized and degraded at a constant rate, resulting in a constant steady-state level. In regulated molecules environmental signals, such as the extracellular availability of a hormone or growth factor, for instance, may cause the rate of synthesis or expression of new surface receptors to increase X-fold. If the rates of outputs are not concurrently and equally regulated by the same factor, then a new steady-state level will be reached, which may or may not return back to normal after the activating signal ceases. Examples of those modifications include: a) gene mutations and other modifications, b) DNA transcription, c) post-transcriptional splicing and other modifications of RNA, and d) translational regulation 9. In the examples provided to illustrate the preferred embodiment of this invention, equations modeling an steady-state approach are used, since biochemical systems are better represented by steady-state than by equilibrium situations. The value for the basal-concentration, basal-density or basal-scaled-amount parameters of each population reflects the physiological steady-state value, when the rate of change is equal to 0 or equivalently when the sum of the inputs equals the sum of the outputs. Concentrations are used in general within classes of bioPools representing soluble entities. However, as it is found empirically in biological systems, most most entities are associated with membranes, with large polymerized structures such as the cytoskeleton or the extracellular-matrix, or associated with one or more other macromolecules forming complexes. This means that the concentration of those bound entities is less relevant than the actual amount of those molecules that are available in the appropriate compartment at a given time, and therefore the term density is used to represent units per compartment. Furthermore, most simulations of biological systems are more meaningful in terms of relative amounts or ratios among the quantities of interacting or regulatory molecules, and therefore the alternative variable called scaled-amount is provided for each bioPool, which is dimensionless and therefore do not require units. The values of the velocities of the generic bioObjects, as provided in the palettes, are computed using the default generic simulation formulas associated with each subclass of velocity variable that is an attribute of each subclass of bioEngine, which by default are dependent on the values of a set of scaled variables and parameters. The user can however select other velocity subclasses from a library provided with this system, each of which has its associated generic simulation formula, and may be dependent on either scaled or absolute values, depending on the subclass.

10. The system of this invention deals with the "incomplete information" characteristic of biological systems by integrating the scaled or semiquantitative values with the absolute values, as discussed in later sections. The scaled-valued variables, such as scaled-amount, have values within the 0.0 to 100.0 scale to normalize the diverse ranges of magnitudes involved in the system. The default initial values of the scaled-basal-amounts vary within this range to best represent the knowledge about the physiological steady-state conditions. As a way of examples: a) a value of 100.0 may model an constitutive abundant enzyme, receptor, or complex-subunit in their inactive form, while this value may decrease at run-time as the value(s) of their active or other derivative(s) increase, so that the total remains 100.0; b) a value of 50.0 may model the normal steady-state catalytic concentration for a constitutive regulated active state of an enzyme, or the steady-state concentration of a substrate, binding protein or ligand, or c) a value close to 0.0 may model any highly regulated induced molecule.

11. Temporal reasoning is important to model and describe the causal mechanisms that drive biological systems. Temporal reasoning is achieved in the system of this invention in several ways:

In general, temporal reasoning is implicit in this real-time system during a simulation, when the values of the variables and many of the parameters vary over time.

Entire contents of BioModels, such as those representing the successive phases of the cell cycle, and other time-submodels within those phases, can be activated and deactivated over time by activating or deactivating the subworkspace of such bioModels, as specified within procedures and rules, at pre-specified simulation time intervals, or based on events generated at runtime, such as a certain variable reaching a threshold value, or a combination of both.

The subworkspaces of specific bioProcesses can be also programmed to be activated for a specified period of time after their activation, as given by its activation-hold-interval attribute. This attribute can be a default value or a value entered by the user or as modified at runtime. This is an alternative to having the control of the inactivation of such subworkspace based on another event. It can also be reasoning by a combination of a given time interval or a given event, whatever comes first, or by events triggering the change of the value of the activation-hold-interval attribute in a pre-specified manner. One such option is to provide a tabular function such as by looking.

12. The types of inhibitions in which a reversible or irreversible complex is formed, such as the binding of an antagonist to a cell-receptor, and the feedback activation or inhibition by secreted products, are all modeled as separate receptor-processes or complex-formation-processes which compete in the background for the amount of cell-receptor available in the common bioPool, according to their respective affinities and concentrations. The reversibility of any binding is usually not explicitly modeled, unless the complex is a target for regulation, and it is implicitly included in the output which is the balance in the predominant direction (as represented by Ks vs. $k_1$ and $k_{-1}$).

13. In fast growing cells or organisms, the dilution factor resulting from cell growth is represented by a parameter $\mu$, while in slow growing cells direct enzyme degradation is more important, since the levels of many enzymes in animal cells is controlled by the balance between enzyme synthesis and degradation, called turnover. The synthesis of an enzyme is represented differently, depending on the available information or the level of detail desired, as a zero-order process or as a first-order or higher-order kinetics, proportional to the concentration of other enzymes or regulators that participate in the complex processes of, while the degradation may have a first-order kinetics proportional to the concentration of enzymes, or or higher-order kinetics, depending also on the concentration of other enzymes or regulators that participate in the regulated degradation process. The total response associated with any particular population of receptors is represented as the maximal activity of a single receptor in the activated state times the receptor density, or scaled-amount, of the bioPool representing that particular compartment.

14. The bioPools representing synthetic agonists, antagonists or inhibitors, such as drugs or toxic substances, have a basal-concentration of 0.0, have no modeled inputs other than the user-entries, and therefore the $\Sigma$ inputs=entry value, at the compartment where it is first introduced. However, it can have several modeled outputs, including the participation in modification-processes and translocation-processes, in addition to the decay term that represents diffusion, degradation and dilution. It is further constrained in that the $[As]*(\mu+\Sigma outputs) \leq [entry]$.

C. ORGANIZATION OF THE SYSTEM, TOOLS AND METHODS OF THIS INVENTION

1. The database, modeling and simulation system object of this invention expands the methods and classes of bioObjects already defined in a previous system, as described in the patent filing with Ser. No. 08/373,992, and builds upon them. The expanded bioObjects comprise additional subclasses of bioEntities, bioPools, bioReservoirs, bioReactants, bioEngines, bioProducts, bioProcesses, and bioModels. More specifically, the additions comprise: a) the new class bioModel and its subclasses at different levels of complexity, b) additional subclasses of existing classes, such as cell-Reservoir and cell-Pool, pertaining to cells, and c) additional attributes or user-menu-choices for existing classes and subclasses pertaining to molecules, which provide additional optional behaviors to, among other things, navigate through the compartments of the biological systems.

2. The current embodiment this system is preferably organized into modules, or large domain-knowledge-bases that represent different biological systems, based on and build upon a core unit referred to in this system as the repository-module, which comprises the definitions of all classes of objects, all the methods associated with them, including among others procedures, rules, formulas and functions, and palettes of a large variety of prebuilt generic bioObjects. The modules can either be independent among them or built upon the knowledge or data contained in a different module, which may run in one or several CPUs. As a way of example, the modules of the Immune System may be based on the Immunology Core module, which contains bioModels generic for the cells and organs of the immune system, and as such it is the basis for other modules which mainly contain bioModels of interacting cells specific for each biomedical field.

3. All the classes of objects comprised in the system of this invention are subclasses of the classes previously defined in the system described in the accompanying patent filing with Ser. No. 08/373,992. Like there, the methods used for inference and simulation are available only trough the developers' interface, and are part of the hidden infrastructure not available for manipulation by the end-users of this system. Parts of the biological information are systematically encoded into the bioObjects, which are the independent knowledge units that can then be repeatedly used as building-blocks by both developers and end-users. The icons that represent the bioObjects can be selected from the menu palettes, cloned, transferred to workspaces and connected. Using the domain-dependent building-blocks, interfaces, and methods designed and built by the developer in Developer Mode, the modeler can expand the library of building-blocks and build complex, application-specific, graphic models of biochemical systems in Modeler Mode. A user can then use those complex graphic models to navigate through those biochemical systems when in Navigation Mode . A user can also use those complex graphic models, in combination with the inference engine and other facilities of the Shell to: a) create dynamic interactive pathways that are context sensitive, and allow more targeted navigation and exploration, or b) perform complex predefined queries, that are context sensitive, and related to structure, relative position in the pathways, function, location in the cell-compartments, or any combination of them, when in General Mode; or b) running quantitative, absolute or scaled, simulations, with the additional use of the Shell's or external simulators, when in Simulation Mode.

4. The description of the present invention will be organized as per the tasks performed in each of the user modes, which are used as headings. Under the heading Developer Mode (Tables 1 through 58), the definitions of the newly defined object classes, as well as the newly methods associated with the high-level classes, will be mentioned and occasionally briefly discussed. Under the heading Modeler Mode, the interface and methods provided to the modeler will be described, with a major emphasis and discussion on how those new tools can be used to create graphic models of very complex systems, using as examples how to handle the challenging aspects encountered when modeling biological behavior. Under the heading General Mode, we will describe the tools and methods provided to the user that wants to interactively explore the system that the modeler has built, and to extract the knowledge incorporated into the system in a variety of forms, including the integration and amplification of that knowledge and the creation of new knowledge by the computer program. A new interface and methods are provided to constraint all the capabilities provided in regard to navigation and pathways creation, to limit the scope of the search to an space selected by the user based on the different new levels of compartmentalization added to this application. This new feature is implemented through new or modified interfaces, such as the Navigation Panel, which can be initiated from a single point of input and dynamically created in association with the desired bioReservoir, or the Experiment Panel, which has been modified to add such capability. Under the heading Simulation Mode, the new methods provided to the user to quantitatively simulate the interactions between the different components within the expanded types of complex models, where the new dimensions of time and space have been added, will be described. Simulations can be initiated as before from a single point of input, through a Simulation Panel dynamically created in association with the desired bioReservoir, or from multiple input points selected by the user through the user-modifiable experiment-panels. However, the design of that panel has been modified to allow selection of the bioModel(s) to be included in the simulation, without needing to transfer them to the Panel. In addition, a new implementation of the simulation procedures has been added, to allow running simulations simultaneously by more that one user, accessing the same copy of the application from different Windows.

D. DEVELOPER MODE: Definitions of Added Building Blocks and their Associated Methods In the descriptions that follow, the references in parenthesis to a Table # points to the definition(s) of the object classes, procedures in pseudo-code form, or other structures that precede the parenthesis, without each time referring to that fact. Those definitions are provided as listings in the form of Tables as an Appendix to this filing.

1. BioModels

In the current embodiment of this invention, any reference to a bioModel means a predefined graphic object that encapsulates in its subworkspace a set of interrelated complex bioObjects, such as bioReservoirs, bioProcesses or other bioModels, representing sets of concurrent or sequential processes. BioModels are used to partitioned the knowledge-base into a modular hierarchy of subworkspaces of bioModels, and can be also described as subsystems or fragments of a larger network of pathways, which can be reused as modules of desired degrees of complexity to be combined in a variety of ways to build larger and diverse systems. The dynamic aspect of a bioModel is equivalent to a system of algebraic and differential equations. BioModels are objects represented by icons, and the constants, parameters, variables and equations that model the system are distributed throughout their component building blocks, which function as distributed parallel processors. BioModels represent empirical biological models derived from experimental descriptive information and semi-quantitative or quantitative data. Very complex bioModels can be build by connecting component parts of an unlimited number of other bioModels by means of connection-posts. The icon of some bioModels, such as sequential time-compartments, may contain stubs to allow connection to other bioModels.

A submodel schematically represents a portion of any size of the network of pathways of a larger structure, such as a cell-bioModel. As the submodel becomes larger, it may be broken down into smaller submodels by simply cloning a new submodel and transferring to its subworkspace the desired bioProcesses and to the subworkspace of its bioReservoir-bin the corresponding bioReservoirs. The connectivity of the pathways is transparent to movements of bioObjects from one bioModel to another, since they are directly connected among them through the structures upon the subworkspaces of bioReservoirs and bioProcesses. The bioReservoirs are located upon the subworkspace of a bioReservoir-bin, which is usually located together with the related bioProcesses within a submodel. However, the bioReactants and bioProducts of any bioProcess that is a component of a bioModel may be connected to bioPosts of bioReservoirs that may be located in the same or in other bioModels. This architecture results in a hierarchy of bioModels encapsulated within other bioModels, which ultimately encapsulate bioProcesses and bioReservoirs, which in turn encapsulate bioReactants, bioEngines and bioProducts, or bioPools, respectively. Although this topology may appear complex, at run-time each of the variables depend on the variables of only those bioObjects directly connected, and therefore the system operates as a set of processors concurrently computing in parallel. The distant connections between the bioModels, bioProcesses and bioReservoirs, established through the bioPosts anywhere in the knowledge-base, interconnect the different schematics into a dynamic multidimensional network of any unlimited complexity. This architecture facilitates the implementation of feedback and forward loops, interactions between components of different pathways, elements that are shared by different pathways, and connections between segments of pathways that are built as separate reusable modules. When one bioPool participates in feedback-loops in two or more pathways, this bioPool may be able to 'switch' from one pathway to the other at a given point, as a result of continuously varying functions, such as different velocities or diffusion rates.

The newly defined subclasses of bioModel are programmed object that represents any physiological system at different levels of structural complexity, such as organ, tissue, cell-interaction, cell, or subcellular organelle, or any other intermediate compartment within those compartments.

Quantitative bioModels are those that represent graphic models which data structures encapsulate mathematical models, representing a set of empirical biochemical models derived from experimental descriptive and semi-quantitative information and quantitative data. The more information is available to model each process of the bioModel, the more precise and compact the overall system will be. In the preferred embodiment of this invention, model parameters are included as object attributes and model-generated results are used as input information for the inference engine. These dynamic models can also reason about the behavior of variables in the past and about the projection of variables into the future. Some of those subclasses of bioModels, such as the sequential time-compartments, can be independently activated and activated by the program during a simulation run. The efficiency of large-scale simulation applications can also be significantly improved using that mechanism, by having whole branches of the model that are not relevant at some point in time deactivated and activated when required, driven by events generated as a result of the simulation itself, or at given time intervals.

Figure 4:
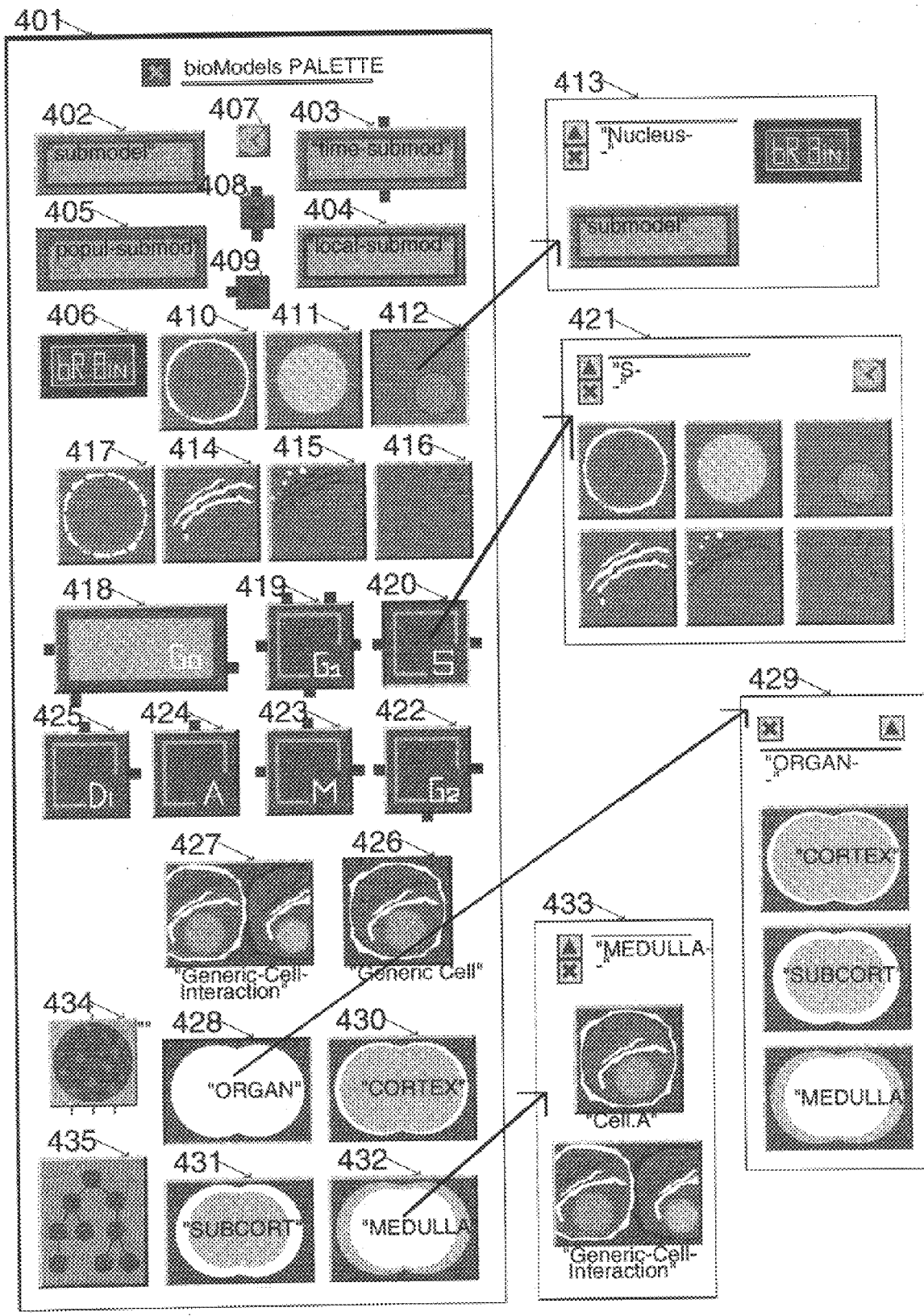
FIG. 4 shows a palette with examples of prebuilt composite domain-specific compartments.

The hierarchy of the class bioModel is shown in Table 1. Various subclasses are defined to represent, as their name indicate, several biological compartments. As shown in FIG. 4, those predefined building blocks are offered to the user in a bioModel Palette (401), and the various classes include: as organ (428, Table 2), organ regions (429–432, Table 3). The differentiation-pathways (435, Table 4) are structures that allow the modeler to manually build differentiation trees, such as the one shown in FIG. 5, which are based on expert-knowledge to represent the sequential progress from one stage of differentiation to the next. The different stages through which a cell lineage goes through is a continuous process, which can be simplified with the representation used in this system consisting of discrete stages that represent different stages of differentiation, defined by characteristic and measurable phenotype, that follow a tree like longitudinal pathways. The cells in those pathways are of the class cell (434, 504, Table 5), and they contain further encapsulated detail, as shown in FIG. 6. A cell contains information in a table of attributes (605, and also encapsulated in its subworkspace, where the different icons are a cell-surface (608), since this is a representation of the cells from the outside, and a set of components that allow that cell to refer a display characteristic markers and receptors that allow them to interact to the outside world, such as the subclasses of extracellular-components (Table 6), the surface-components (613, Table 7), secreted-components (617, Table 8), and specific systemic-components (612, Table 9) in their environment to which they respond. Each of those components have a set of attributes, as shown in detail in their open tables of attributes shown for each of them (611, 620, 633, and (616), which allows them to refer to either specific bioEntities (624), bioReservoirs (626) and bioProcesses (628) in the interior of a cell-bioModel that contain the mechanistic pathways. Note that, as shown in FIG. 7, a cell-interaction (427, 703, Table 1) encapsulates the interaction of two cells 703 and 704, that use the same type of graphic extracellular-components to interact with each other directly (705 and 706), through the components that one secretes (707) and for which the other has specific receptors (708), and both interact with their environment through specific receptors (709) for systemic-components (710). Clicking on those icons displays their menu (not shown) from which options, the user can select the display of a variety of other graphic associated structures, as indicated earlier for specific attributes. The different menu-options, and their associated procedures are listed in Table 10 through 14). Tables 15 and 16 list functions that allows the modeler to automate the task of establishing the distant connections to those graphic structures. The interacting-cells (703 and 704, Table 18) in this interface do not contain a mechanistic model of its components, but rather refers to and displays another cell-bioModel that store those mechanistic models. In this way, this structure is used as an interface to design interactions between other cell-bioModel, and new cells and other connections to bioProcesses or bioReservoirs can be establish. The external components, such as serum or incubation media, or single or lumped toxic-byproducts, for which there are specified or lumped receptors are represented by a set of bioReservoirs, such as RPMI-Pool, serum-Pool, are connected to a bioProcess with a receptor-engine that has at least one bioProduct connected with one of the bioReservoirs within the cell. The function of the bioEngine is to compute the consumption an exhaustion of nutrients at a rate proportional to $\mu$, the specific growth rate. The byproduct-Pool's concentration is used in turn to modify the value of $\mu$ by multiplying it by a parameter $0<m<1$.

The class cell-bioModel (426, Table 20) as a subclass of bioModel is used to represent a cell as observed from the inside, that is as a container of subcellular compartments, that in turn may contain different layers of submodels until at the end of the compartment hierarchy, the bioReservoirs and bioProcesses are contained. Cell-bioModels are used for modeling prototypic cells of interest in a very detailed way through their functional structural components, which are constructed graphically through the various levels of other encapsulated bioModel that a cell-bioModel may contain in its subworkspace, but which at the end contain variables and parameters that allow to quantitatively simulate those models, or more realistically, constrained submodels within the cell, which can be selected by selecting any of the compartments at any desired level. The hierarchical encapsulated allows not only to display different levels of detail to focus only those parts of the system that are relevant to the user at any given time, but also allow to expand the model adding additional levels of detail whenever desired. Each cell-bioModel or any of its contained BioModels can be used as modules to build other bioModels with increasing degree of complexity. This modular and reusable building block structure gives the system great flexibility and transparency, while allowing to build very complex cell-entities.

Figure 8:
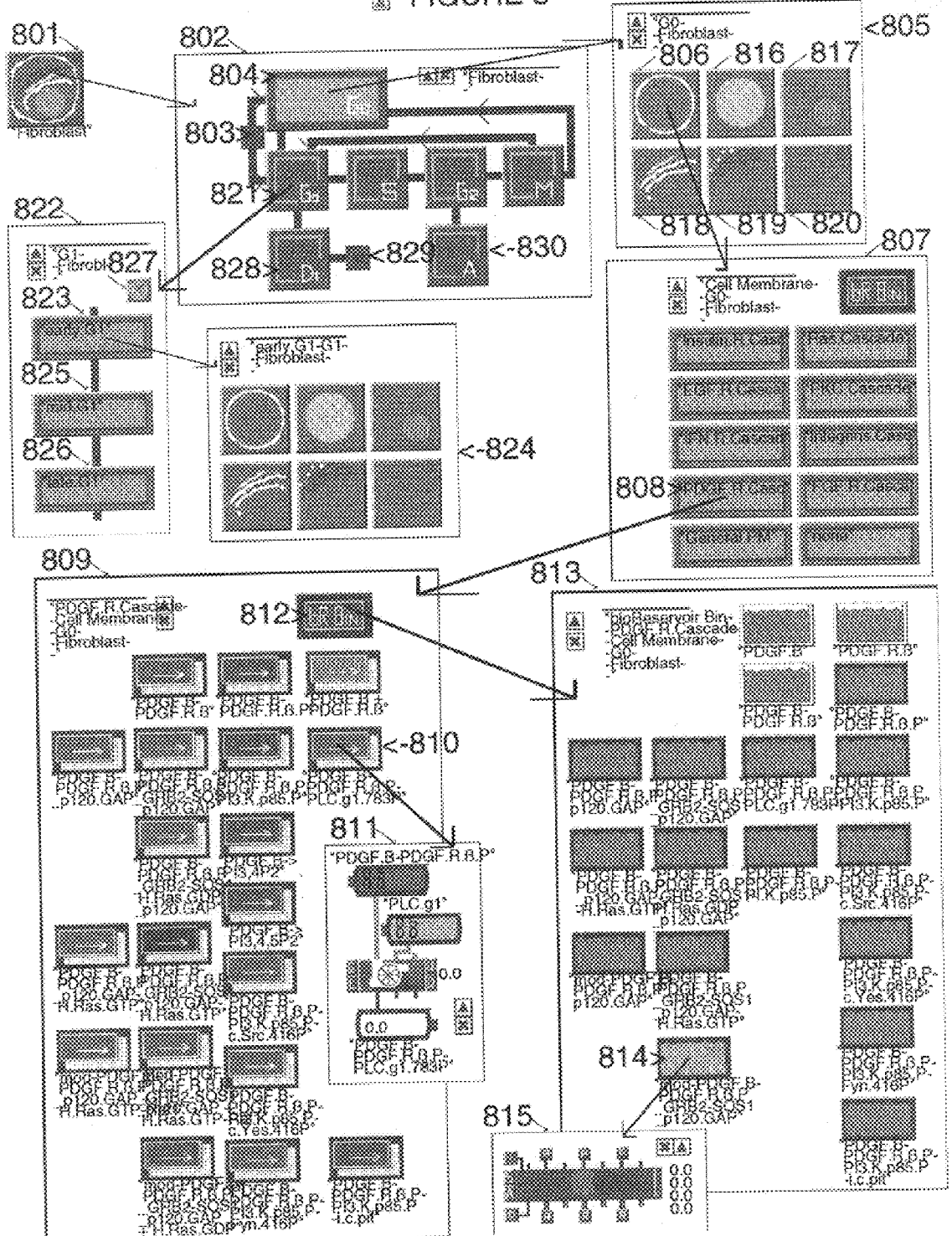
FIG. 8 describes a domain-specific compartmentalization of the components of a hierarchical model, in this case focusing on the sequential phase of a cell's cycle and on its subcellular compartments.

As shown in FIG. 8, each cell-bioModel (801) has a subworkspace (802) upon which are represented the characteristic phases of the cell cycle (821), that follow a repeated cyclic pathway, or the cell differentiate into a different stage (828), or may go into apoptosis (830), a terminal stage. Those cell-phases (418 through 425, Table 24) are the main type of time-compartment (Table 23) defined in the current implementation of this invention, but other types of compartmentalization are also possible by means of the time-submodels (403, 823–826, Table 23). The biomodel-posts (803, 829, Table 25), ant its associated methods (Table 26) allow to connect those cell-phases with another cells-phases upon other cell-bioModel, and to display them.

G0-compartment: (418, 804) in cell biology the G0-phase represents resting-cells. In the current embodiment of this invention, this compartment also represents the background processes of resting-cells, but in addition it also contains all those background bioProcesses that are not specific for any particular phase of the cell-cycle or which cross-over the boundaries of several of those phases. This compartment is frequently the starting point of a simulation and its bioPools are usually modeled by the default "normal" steady-state values of the variables and parameters of interest.

G1-phase-compartment: (419) represents a state of cells after they have been activated by external factors, and may be further compartmentalized into two or more time-compartments. For example: the G1.1-compartment represents activated-cells or early-G1-phase-cells which have recently entered the G1-phase of the cell cycle, as characterized by transcription of early-response genes, expression of new receptors; while the G1.2-compartment or late-G1-phase-cells, is characterized by transcription of late-response genes or increased secretion of specific cytokines or other signaling factors S-phase-compartment: (420) represents the state of cells in S-phase, characterized by DNA synthesis;

G2-compartment: (422) represent cells in the G2-phase, characterized by double DNA content and before entering mitosis;

M-compartment: (423) represents cells in the M-phase, during the mitotic process;

Di-compartment: (425) represents cells entering a new differentiation stage, when a different set of activated early-response and/or late response genes induce permanent changes in the types of genes expressed. This layer is followed, depending on the combination and strength of signals provided by simulation events, by either the G0-compartment, or both this and the G1-compartment, of the next cell type in the differentiation pathway.

Ap-compartment: (424) apoptotic cells, when cells in the G1.1-layer do not receive the appropriate signals to enter either the G2.2-layer or the DI-layer. This is a terminal layer which only effect is to reduce the size of the total cell population. (Note that the total cell population size is increased at the transition after every M-layer, by an amount equal to the size of the population in that M-layer. Also note that there is a non-specifically-modeled overall cell death that is represented by a decay parameter, which is adjusted during training to fit the experimental data.

The default time-duration of each of these temporal layers is set according to experimentally obtained knowledge of such duration, under specified "normal" conditions. A layer-rate-constant, $\tau_1$, is constrained to values $-1 > \tau_1 > 1$ and initially set to 0. When the effects of different combinations and strength of signals on the duration of any of the layers are measured, then the value of $\tau_1$ is adjusted to fit the target values of the training set→$t_l = t_o (1 + \tau_1)$.

Each time-compartment (804, 823) encapsulate (805, 824) several spatial compartments that run in parallel to each other, and which represent the clearly defined subcellular compartments, called cell-Compartments (Table 27), such as the cell-membrane (806), cytoplasm (816), nucleus(817), endoplasmic-reticulum(818), Golgi apparatus(819), endosomes(820), mitochondria, and so on. Each of the cell-Compartments comprises a subworkspace (807) which in turn may contain various submodels (808). Other local-submodels (404, Table 28) are also provided for other types of spatial compartmentalization. The subworkspace (809) of a submodel may contain other submodels (not shown), and submodels may also contain bioProcesses (810) or bioReservoirs (not shown). In the current embodiment, the bioReservoirs (814) are preferentially hidden in a bioReservoirs-bin (406, 812, Table) that belongs to that bioModel.

The connections between the time compartments, called cycle-path (Table 30), contain a number of parameters and variables to hold the values of the rate-constant and the progression rate, that can be used when developing quantitative models for simulation purposes. A number of other variables and parameters that describe among others: a) the size related attributes of the cells, and b) quantities related to population dynamics, such as those shown in FIG. 2, (217–220), which are attributes of the cell-phases, are defined in Tables 31 through 34. A collection of inference blocks and related structures that may be used to control the activation and deactivation of the time compartments, at intervals that are predefined or dynamically computed depending on simulated variables are also defined (Tables 36–38). Table 39 lists as an example a set of simulation formulas for state variables that can be used to compute the dynamic changes in cell numbers that are accumulation in each of the cell-phase, when using these graphic structures in combination with a population dynamics approach. Furthermore, Table 40 lists a set of rules that can be alternatively used to control the progression through those cell-phases, when using the mechanistic approach. As the reader may realized, there are a number of different alternatives, encapsulated within those graphic building blocks, to model the complex systems at different levels, as discussed in the modeling section.

FIG. 8 shows the major states are considered in the currently preferred embodiment of this invention, following the classical nomenclature and concepts generally accepted in the scientific community, the resting state is defined as the Go phase. Each of the values of the "cell-phase" attribute of a cell-bioModel, indicates which of those phases is currently activated, if any in addition to the G0-phase. While at Go, if the cell is activated by a growth factor, antigen or any other activating stimulus, the cell enters the activated state or G1, from which it can follow to other phases of the cell cycle or the differentiating states, depending on the signals received. G1 is bounded by the progression signal or cell birth and the initiation of DNA replication, and characterized by sequential expression of additional genes, protein synthesis and cell growth. S is bounded by initiation and completion of DNA synthesis. G2 is bounded by the completion of DNA synthesis and the initiation of mitosis, and characterized by further cell growth and/or protein secretion. M is bounded by initiation of mitosis and completion of cell division, usually represent about 2% of the total. Although the cell cycle is a continuous one, it can be compartmentalized into functional cycle intervals whenever it is deemed useful to better represent the dynamic simulation of the system.

Figure 5:
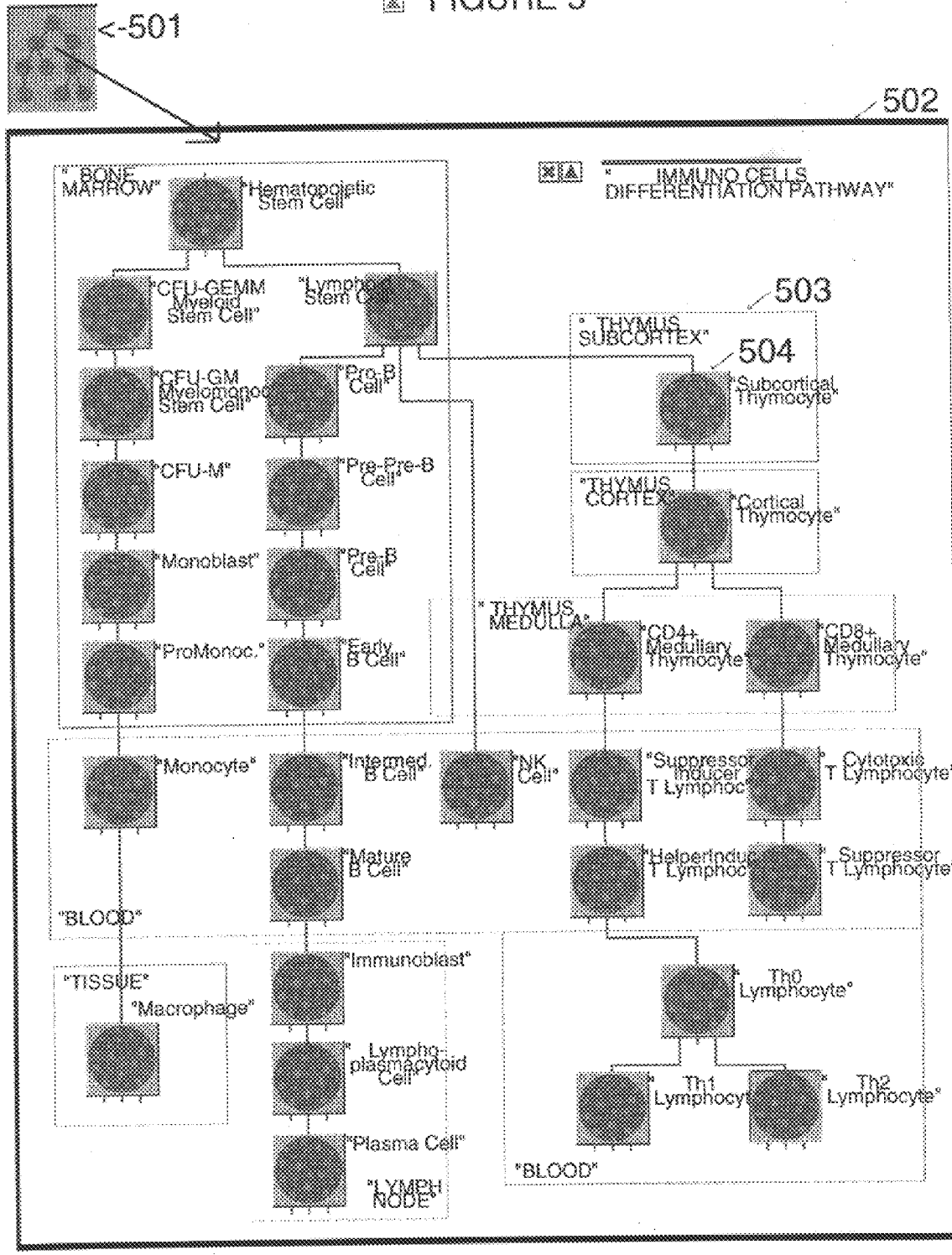
FIG. 5 describes a domain-specific implementation of an evolutionary tree representing the alternative successive states that an iconic compartmentalized model may follow depending on the events that depend on their internal processes responding to the environment, from an external point of view.
Figure 6:
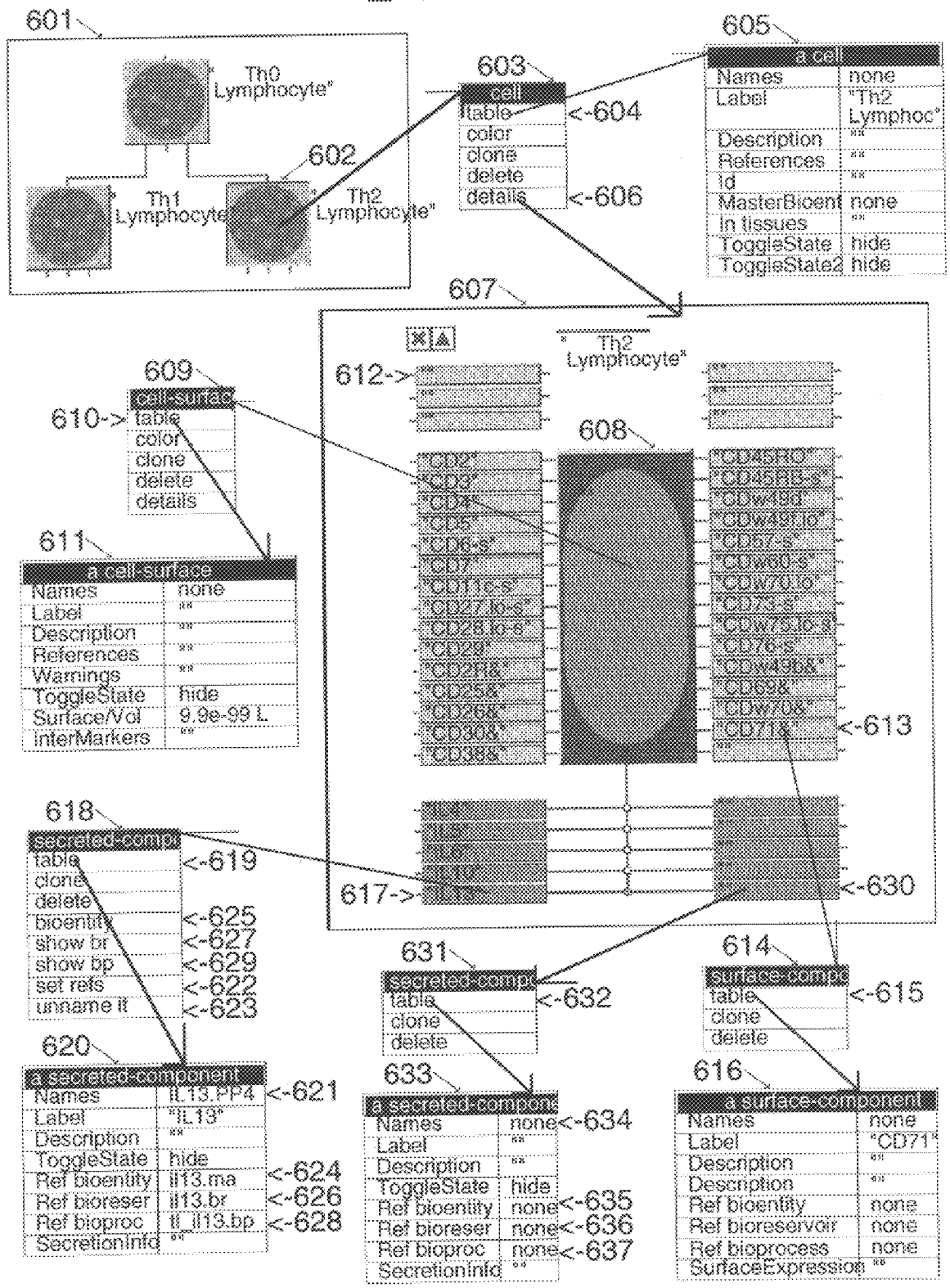
FIG. 6 describes a domain-specific characterization of the iconic compartmentalized model from an external point of view, with the table of attributes of various of its componets.
Figure 7:
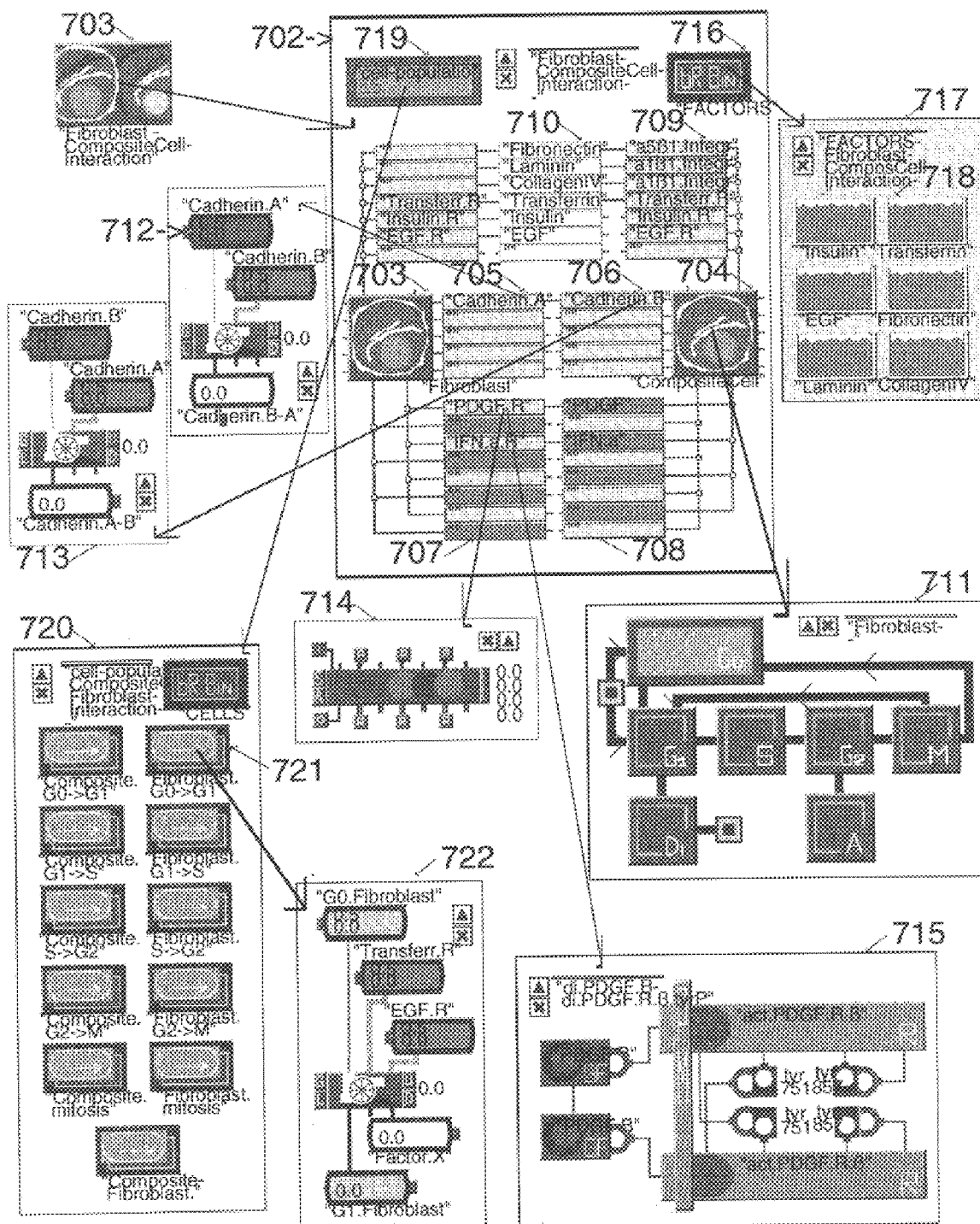
FIG. 7 describes a domain-specific implementation of compartmentalized model interacting with each other and with the external environment.

As shown in FIGS. 4 through 6, there are switching points where the cell has to decide between the differentiation and the cyclic pathways resulting in a variety of different patterns that depend on both the internal stage of the cells and other components in the system, external to the cells. A typical pattern results in: a) cells in the resting stage, when the steady-state conditions are assumed, then after activation by specific external signals, switching through the cycling phases one or more cycles, or back to resting, then after activation by specific external signals during one of those stages, switching to one of the next nodes in the tree, committing themselves to that branch of the tree in the longitudinal pathway, then once at the new node they may go back to a) for a period of time, in a resting stage during which the new steady-state conditions are assumed, or, if activated by specific external signals they may go back to b) with the new steady-state conditions as the base-line.

2. BioEntities

In the current embodiment of this invention cells are defined in two different ways, as a subclass of bioModel composed of cell-Compartments, as described below, and as the class cell (Table 1), a subclass of bioEntity used to represent a cell as observed from the outside, and including any defined, mostly external, characteristics that can be used to assigning that cell to one type of cells and to distinguish it from cells of other types. The class cell is further classified according to a branching differentiation tree, when known. Some of the characteristics common to each class are defined and inherited as attributes, and the instances are used to define the many nuances between that differentiate them from each other, particularly when following the almost continuous differentiation process. The definition templates (not shown) are used to specify attributes that are successively added, through the definition templates, to the definitions of each class and its subclasses. For instance, a cytotoxic-T-lymphocyte has, in addition to any attribute specific to its class, all the attributes of T-lymphocyte, lymphocyte, hematopoietic cell, cell, and bioEntity, and therefore they have to be encoded only once. By default, four sets of stubs, one each on top, right, bottom and left of icons, are defined for cells to allow for branching when building differentiation-pathway, as described below. An instance of cell may correspond to an instance of cell-bioModel. One of the menu options of this class is "biomodel" which upon selection by the user displays the subworkspace of the bioModel referred to by one of its attributes, "ref-biomodel", if any, and that option is only visible when such attribute has a value. Other subclasses of membrane, are used to represent interactions of several types of cellular membranes with other molecules, which are used, as described in the accompanying filing with Ser. No. 08/373,992, to build the graphic structures upon the subworkspaces of other bioEntities.

Other subclasses of membrane, are used to represent interactions of several types of cellular membranes with other molecules, which are used, as described in the accompanying filing, to build the graphic structures upon the subworkspaces of other bioEntities.

The incubation medium may be considered as a whole, as a lumped bioEntity, or any of its components may be schematically modeled, lumping the remainder, such as basal-medium and other required nutrients with their associated values, such as concentrations or percentages.

3. BioReservoirs

Figure 9:
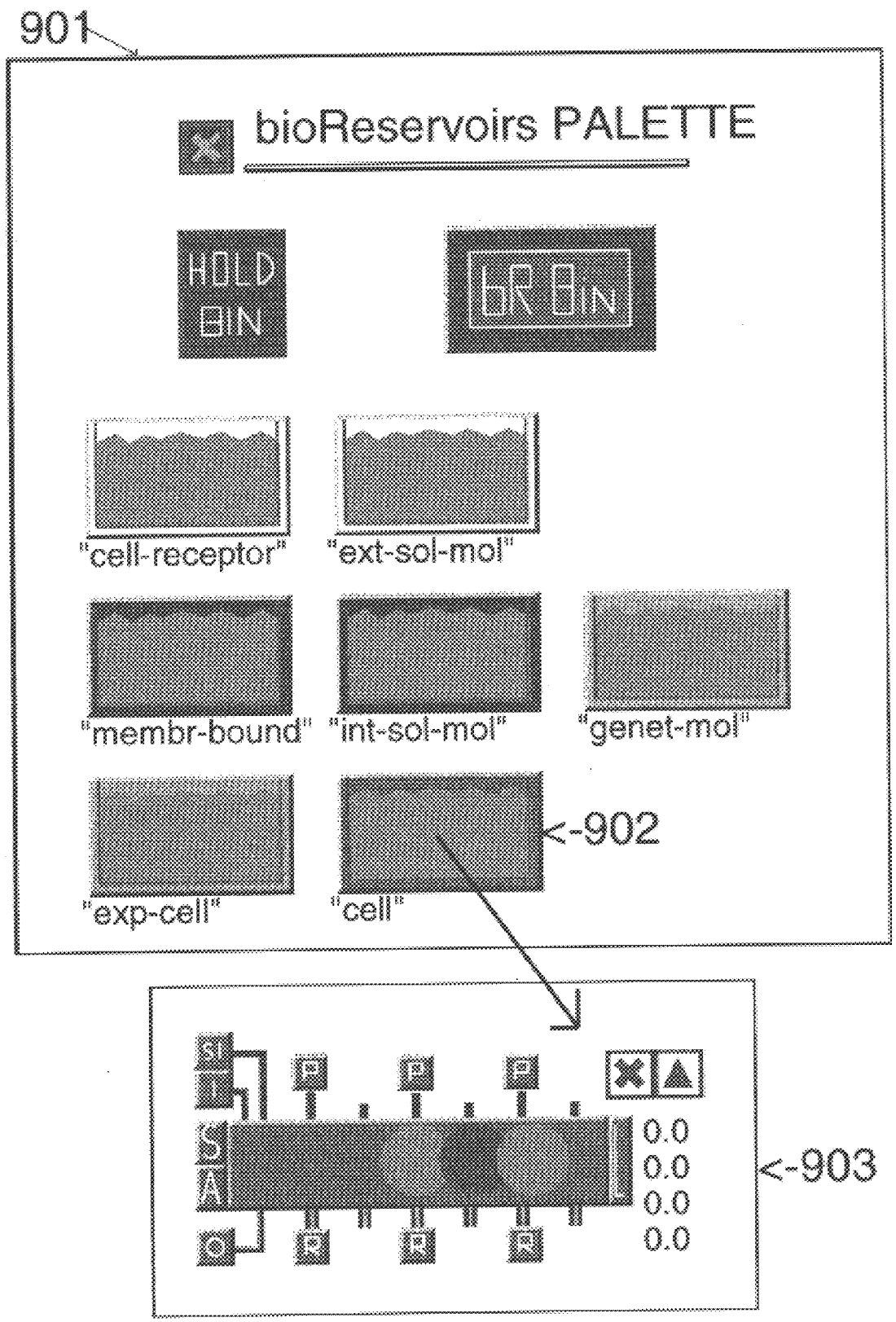
FIG. 9 shows a palette of reservoirs, accessible from the domain menus, further focusing on a view of the subworkspace of one of them with its iconic components, comprising a pool of entities and its inputs and outputs with its components.

A number of new subclasses (FIG. 9, Table 42 and 43, FIG. 9) of bioReservoir such as: cellReservoir, exp-cellReservoir, genet-mol-Reservoir, as well as subclasses of sol-mol-Reservoir, and bound-mol-Reservoir to represent new concepts needed for this application. The corresponding new subclasses (Table 44–46) of bioPools also have been defined. A cell-reservoir represents a container for a specific cellPool, which in turn represents a number of cells of the same type, and the same state if so desired by the modeler. The ref-bioentity attribute of several bioReservoirs may point to the same bioEntity, to represent populations of the same entity in different locations or points in time. This feature results in a reduction of the size of the knowledge-base, by keeping the descriptive qualitative, structural, and functional information of a bioEntity separate from the configurable additional quantitative information that characterizes each bioReservoir.

As in the accompanying filing with Ser. No. 08/373,992, a cellPool can be simultaneously represented in different bioProcesses by either a bioReactant or a bioProduct, to which it is connected via a r-post or a p-post, respectively, keeping the connectivity of the schematics. Among the functions of a cellReservoir and its cellPool are: a) to simultaneously connect all bioProcess in which such cellPool participates, to allow all those bioProcesses in the same compartment to concurrently compete for the quantity of the cellPool available at that point in time in that compartment; and b)to hold the pointer to the specific bioEntity that populates that pool, the quantitative parameters and attributes that characterize that particular pool, and the variables that dynamically compute the quantity of the corresponding bioEntity in that particular pool. cellReservoir serves as the point of entry for inputs from the user, or other external sources.

4. BioProcesses

The only new subclass of bioProcess is cell-bioProcess (Table 51). As shown in FIG. 12 in the current embodiment of this invention, a cell-bioProcess may contain bioReactants and bioProduct that represent pools of cells, in addition to containing bioReactants and bioProduct that represent pools of chemicals. So it is possible to have bioProcesses where molecules interacting with molecules, as well as cell-bioProcesses with molecules interacting with cells (1205), or cells interacting with cells (1211). In addition, there may be a set of interacting-cells as a result of interactions of cells (1214). As in the accompanying filing, sets of bioProcesses may be distantly connected through the corresponding bioReservoirs to define a multidimensional network of biochemical pathways. The connections between bioEngines an the bioPools ocurr as each bioReactant and bioProduct is connected distantly to the bioPool it represents through a bioPost. Like in biological systems, some bioProcesses are relatively simple, and some may become very complicated, but all are built with basic building blocks.

Figure 10:
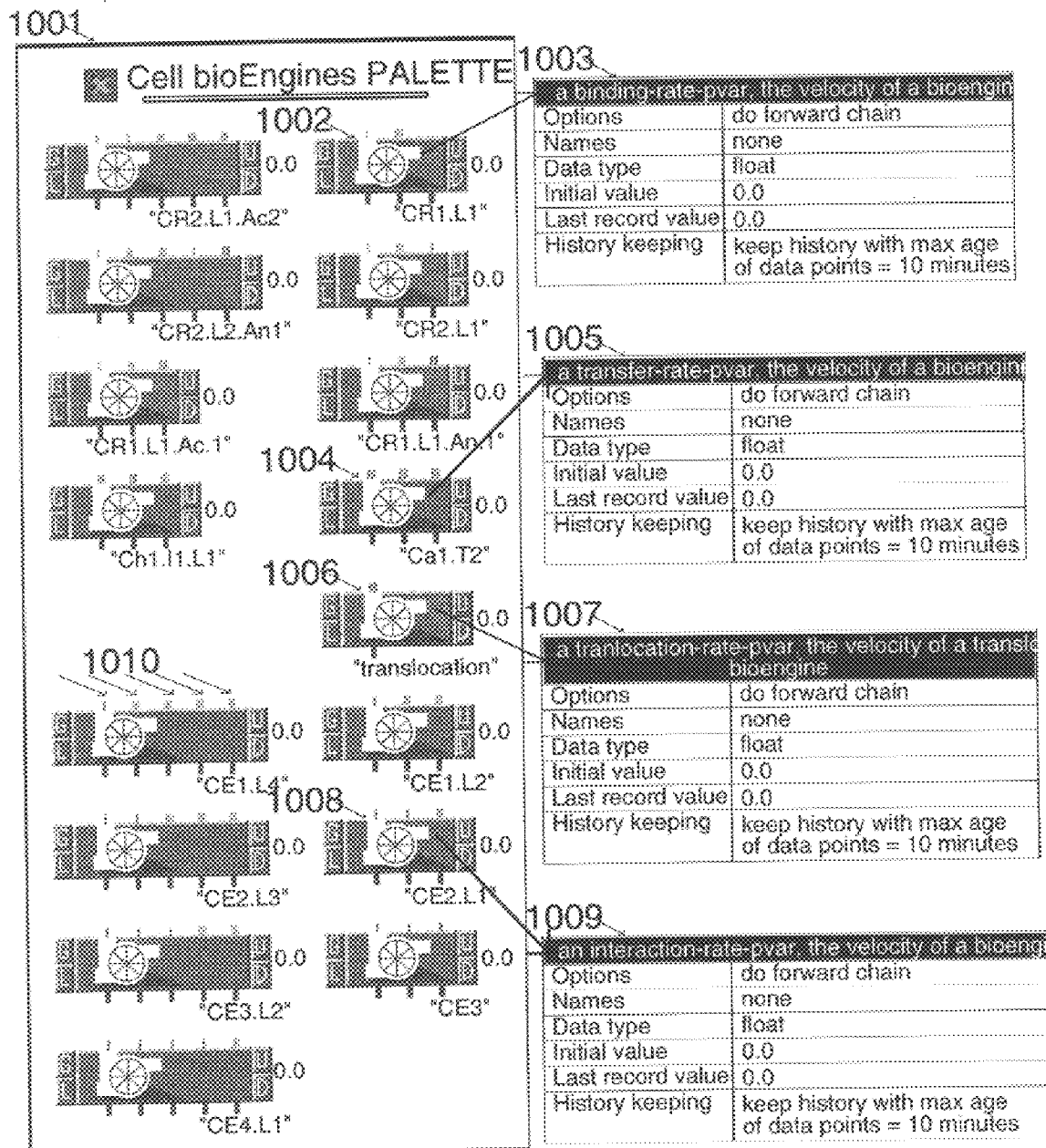
FIG. 10 shows a palette accessible from the domain menus, with examples of prebuilt engines and the table of attributes of the instances of different predefined classes of variables, with associated generic simulation formulas associated with each class, that provides the simulated values for a velocity attribute.

Additional type of bioProcesses are those that represent translocation processes between location compartments, where the bioReactant represents a fraction of a given bioPool in a given compartment, is removed from that bioPool and transferred, with a time-lag equal or larger than 0, to the end bioPool which is connected to the bioProduct, and which represents a different pool the same entity in a different compartment. These types of bioProcesses contain subclasses on bioEngines newly defined (FIG. 10, Table 52–55). The class cell-bioEngine (Table 53), which is a subclass of bioEngine, has several subclasses, as shown if FIG. 10, which differ mainly in two characteristics: the number of stubs that define the specific connections to the different classes of bioReactants and the formula associated with its Velocity.

In the physiological modular bioModels of the system of this invention, the known pathways are described schematically through the bioProcesses, which are integrated through the bioReservoirs. The metabolic pathways of cells and organisms are composed of a large number of chemical reactions and compounds, that, assuming normal physiological conditions, maintain the steady-state of the system. As shown in FIG. 12, and to simplify the overall structure of the system, in the currently preferred embodiment of this invention it is possible to consider many of such metabolic pathways as black-box-bioProcesses with inputs and outputs connected to other modeled pathways or two other black-box-bioProcesses, which are not modeled in detail. If and when it is desired to model disturbances at specific points in the pathway represented by a black-box-bioProcess, it can be split into the pathway before and the pathway after the regulated location, which is represented by a normal bioProcess, with the two new pathway segments now represented by two new black-box-bioProcesses, and the segment where the disturbance occurs to be defined and modeled.

In addition, it may be desirable to model a pathway as a single lumped bioProcess. Such may be the case for an enzymatic pathway for which: a) the details may be unknown or not desired, b) only the inputs and the outputs are relevant, and c) sufficient quantitative or qualitative information is available about the rate limiting enzymes and the inputs. Because of metabolic and energy/mass conservation constraints, only a few of their net conversion rates are independent variables, and the others are mutually dependent, various of those reactions can be combined and the pseudo-steady-state approximation of the combined process can be used instead. For these cases, the currently preferred embodiment of this invention provides enzyme-bioProcess subclasses with two or more enzyme-bioReactants, with velocity variables which associated formulas consider only those enzymes, together with the substrates that are inputs to the pathway and the products are outputs of the pathway, ignoring the intermediaries and other participating enzymes. The following are examples of overall rates of synthesis resulting in the production of a cytokine, IL2, as a cellular response to its binding of another extracellularly provided cytokine, IFN-α, that could be represented by a set of bioReservoirs and bioProcesses, to represent each of the terms of the equation.

$$rs(\text{TF-IFN-}\alpha) = k1 * [\text{IFN-}\alpha]$$

and $$rs(\text{mRNA-IL2}) = k2 * [\text{TF-IFN-}\alpha];$$

or $$rs(\text{mRNA-IL2}) = 1 + ka[\text{IFN-}\alpha]/1 + ka[\text{IFN-}\alpha] + ks;$$

$$rs(\text{IL2}) = k3 * [\text{mRNAIL2}];$$

Figure 11:
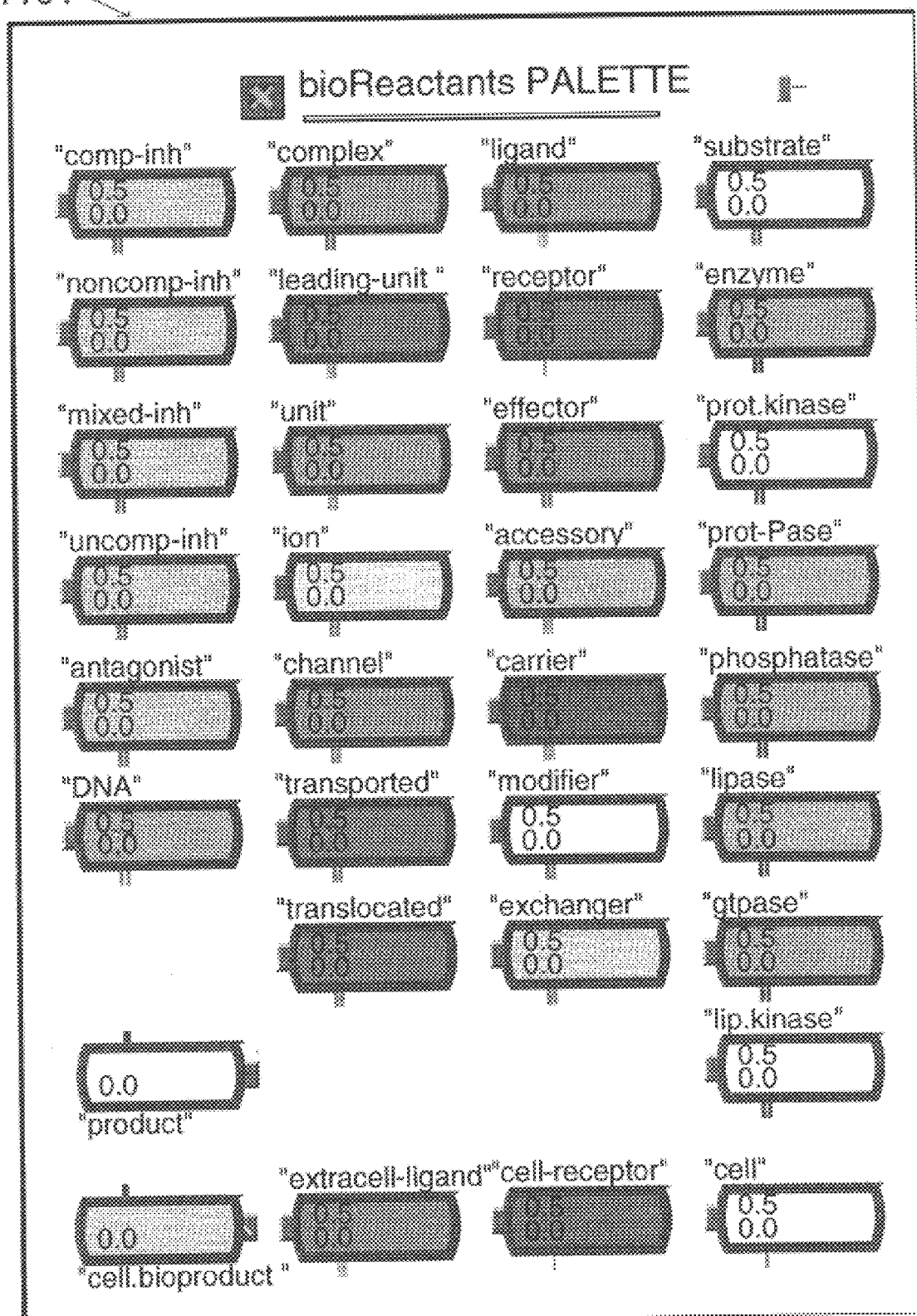

New subclasses (FIG. 11, Table 56–57) of bioReactant are also defined, such cellReactant, cell-receptor, extracell-ligand, to represent the new roles for cells or molecules required in this application, as well as a cell-bioProduct (Table 58) subclass of bioProduct. As with other classes of bioReactants, each cellReactant has a Contribution, given by a variable that can take values from 0.00 to 1.00, and represents a dimensionless scaled 5. BioPosts In the current embodiment of this invention, any reference to a connection means an object that connects other types of bioObjects. Connections can be represented graphically by the union of the stubs of the bioObjects when upon the same workspace, or invisibly when the bioObjects are upon different workspaces, in which case they are referred to as distant connections. Different types of connections are defined to constraint different types of relationships. The definitions of bioPools, bioReactants, and bioEngines, among others. prescribe the class of connections that are allowed at each named port, as defined in their stubs attribute. Different links, inputs and outputs are represented graphically by different classes of stubs which the user can click and drag to create new connections. Stubs are color and pattern coded to represent the different types.

6. Varied Structures:

BioReservoirs which variables have scaled values can be mixed in a simulation with BioReservoirs which variables have quantitative values, since both types of outputs are integrated at the bioProcess level only after being transformed to a scaled value. However, the output values of the variables of BioReservoirs and of the thresholding parameters, such as Km, Kd, Ki or kp, have to be of the same type, either quantitative or scaled. The choice of scaled values between 0.0 and 100.0 for basal-Concentration, based on the knowledge of the domain expert, can also be entered manually within the table of attributes of the bioReservoir.

Tabular functions of one argument allow to deal with situations when the algebraic relationship between two bioVariables is not known, but experimental data is available to build a table that relates a set of values that represents the magnitude of a cause with the set of values that represents the magnitude of the corresponding mechanistic effects or cellular responses, and straight-line interpolation is optional. These are important tools to biologist who frequently measure complex cellular responses to external factors.

The dynamic reasoning used for query, navigation, and simulation depend heavily in the use of relations, in addition to the graphical connections. Physical and abstract relationships between two objects may be represented through relations which, after being defined by the developer, may be dynamically and transiently created at run-time by the inference engine. The existence of relations can be concluded and reasoned about, and the existing relations for a particular object can be also be listed using the "describe" option. Most of the relations are created during the initialization set of procedures, while others are created at run-time by the sets of procedures used during query, navigation, and simulation. The creation or breaking of relations are treated as events that are forward chained to rules that refer to the relations in their antecedent.

E. MODELER MODE: Handling Challenging Aspects of Modeling Complex Systems' Behavior 1. Modeling Internal Mechanisms of Cells The transfer of molecules from compartment i to compartment j (Figures) does not happen at once, but rather follows a Gaussian distribution, which may be modeled using the corresponding model-block to from which the translocation-rate would be dependent. The bioEngines have also a "time-lag" attribute, defined as the time interval between the availability of the bioReactants to the bioProcess and the the availability of the bioProducts to the next bioPool, which can be used for processes where translocations of molecules or cells are involved. The analytic equations for the distribution of bioEntities in consecutive pools, are a function of the initial concentration of the first bioPool and the corresponding translocation-rate constant (k) and time-delays (d), respectively, of the successive bioEngines. For example, to model the series of translocations of proteins through the several compartments in which they are processed after their synthesis, with the system of this invention, the modeler would clone from the Palettes set of bioReservoirs and bioProcesses of the appropriate types o represent the different terms of the following equations, which are then transferred to the appropriate compartments, connected and configured, and desired values are given to the model parameters. Translocation rates between compartments could be expressed as translocation half-times, defined as : $t_{1/2}$, nu=In $(2/K_{nu})$, where $K_{nu}$ is the rate constant for processing in the nucleus or the rate constant for transport from the nucleus to the ER, or both lumped together. For steady-state balanced growth, where $\mu=0$ and rp(t) is the rate of transcription in the nucleus (molecules/hour/cell): $[RNA]_{nu,ss}(t)=rp(t)/K_{nu}$. The additional equations that follow are similar to those proposed for cell cycle-dependent protein accumulation by Bibila & Flickinger, (1991), Biotechnology and Bioengineering 38: 767–780, and have to be adapted for use in the simulation formulas of the system of this invention which takes a dynamic approach:

$$[X_1]=\$X_1*[X_1]_o*e^{-k1*t}\text{(this is ER)}$$

$$[X_2]=\$X_2/\$X_1*[X_1]_o*(e^{-k1*t'}-e^{-k2*t'})*k_1/(k_2-k_1),$$

where $t'=t-d_1$ (this is Golgi)

$$[X_3]=\$X_2/\$X_1*[X_1]_o*(-(e^{-k1*t''}-1)/k_1+(e^{-k2*t''}-1)/k_1)/(k_2-k_1),$$

where $t''=t-d_1-d_2$ (this is extracell. comp. for secreted proteins)

On many occasions, the newly generated molecules are secreted (617, 707), while on other occasions, the newly generated molecules are retained in the cell (613, 706, 708, 709), either to maintain housekeeping functions, which are usually included in the steady-state and no implicitly modeled, or they result in new cellular functions, in which case, its mechanisms are graphically modeled (809, 813). If this response results only in proliferation, the inference engine may monitor the simulation of the cell mechanisms, and based on the values of certain variable or sets of variable, may cyclically activate the next phase-compartment in the cycle (802). However, if the response results in cellular differentiation, the inference engine activates a different cell-bioModel 180; if such exits, that represents the new stage of differentiation, or will send a message to the user otherwise.

The different bioProcesses in a cellular bioModel may be activated for different periods of time, if placed within sequential time compartments, but they will be overlapping with many other bioProcesses (809) contained in the G0-compartment, which are not deactivated during a simulation. BioReservoirs (813) that may be participate in two different sequential time compartments are preferably located and contained within the G0-compartment, to maintain the continuity and to carry over the values of its concentration/density/scaled-amount from one sequential discrete time compartment to the next. These temporal compartments represent somewhat defined cellular phases with different activities.

Mechanisms (809, 813) that are well studied in one animal species can be interpolated in the pathways of other species where the pathway may be less understood, such as in humans, by cloning the submodel (808) containing the bioReservoirs (813) and bioProcesses (809) from the first species and transferring to the appropriate compartment (806) of the second, and then renaming and reestablishing the appropriate connections. For instance, the genes that participate in programmed cell death or apoptosis in the nematode C. elegans have been identified, and it appears that ced-9 acts by inhibiting ced-3 or ced-4 activity. Since the human bcl-2 is also active when inserted into C. elegans (Vaux et al., Science 258: 1955) and it is also believed to be the homologue of ced-9, a model equivalent for that for the interactions of ced-9 with ced-4 or ced-4 can be also constructed for bcl-2 with ced-3-like or ced-4-like.

BioPools that represent points of entry for non-physiological substances, such as drugs or synthetic agonists, antagonists or inhibitors that are not produced within the cells, at the compartment where it is first introduced have the following characteristics: a) they receive their values only from external sources, such as a simulation-panel, initially, the concentration equals the external input, and therefore $\Sigma$ inputs=entry Value; b) they have a basalConcentration value of 0, c) they have no schematically modeled inputs, d) e) they may have several schematically modeled outputs, through modification- and translocation-bioProcesses, in addition to the decay term that represents diffusion, degradation and dilution, and e) the quantity variables of those bioPools cannot obtain values higher than those inputed by the user, but may get smaller over time due to the outputs and the decay factor $([As]*(\mu+\Sigma \text{outputs})\leq[entry])$. When that compound is modified or translocated to another compartment, the latter's is a regular bioPool, but still constrained 2. Modeling Cell Population Dynamics There is a number of ways of modeling and simulating cell population dynamics, using the current embodiment of this invention. A number of attributes defined for the classes cellReservoir, cellPool, cell bioModel, and other bioObjects can be used to hold parameters and variables to be used for that purposes. Following the teachings of this invention, other attributes can be similarly defined and used to better meet any particular biological system to be modeled, or hypothesis that a user may want to test, or to meet the needs for any monitoring or control system that use those biological models. Some examples are presented below.

Figure 14:
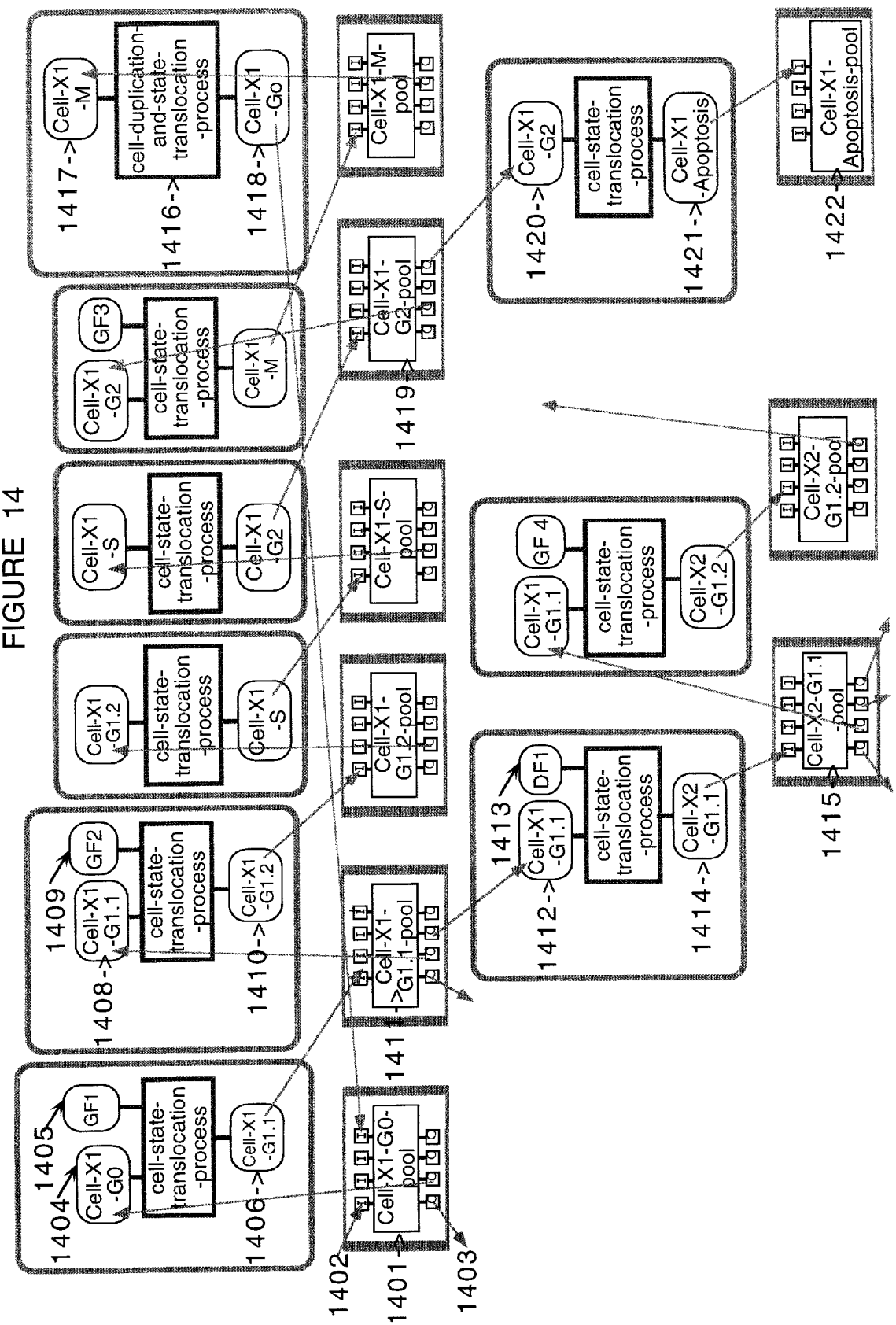
FIG. 14 is a detailed representation of how in this invention pools of cells interact with pools of molecules as reactants of processes which products are either molecules or in a different state.

As shown in FIGS. 3, 12 and 14, the state transitions are represented in the system of this invention by translocation bioProcesses between two bioPools, each containing entities in the former and in the latter states, at a rate that is determined with one of three approaches: a) mechanistic approach; b) probabilistic approach; or c) deterministic approach.

In the mechanistic approach, the rate of the translocation process will be dependent on the dynamically changing values of certain variable or combination of variables, implicitly modeled inside an indicated cell-bioModel, reaching some threshold value(s), as shown in FIG. 3. With this approach, the high-level models may be integrated with the mechanistic models, representing both the spatio-temporal integration in a single cell-bioModel and the quantitative data about populations of such cell modeled. This mechanistic approach is currently difficult to implement for the particular domain selected for the current embodiment of this invention, since there is not sufficient information available. This approach can be implemented with better known systems in other domains.

For some simplified in vitro biological systems, such as oocyte extracts, a mechanistic approach is used to model a transition which mechanism is known or expected, such as the role of the interplay between cyclin-B2 and the phosphorylated and dephosphorylated forms of the cdc2-kinase in the transition from the G2 to the mitosis phases of the cell cycle. The rate of increase in the number of cells with a cdc2**cyclin (cc)level greater that $\phi$ in a given cell cycle phase=fraction of cells in that phase $(G_1)$ * {the rate at which cells within that phase reach a cdc2cyclin level $([cc]^{G1})$ greater that $\phi$—the rate at which cells with cdc2cyclin level greater that $\phi$ leaves that phase }.

The following is an example of how a simplified mechanistic approach can be implemented. The rates of growth in eukaryotes and the rates of translocation from one cell-state-pool to the next can be represented as a linear or non-linear functions of the concentrations of specific molecules, such as external regulatory factors, regulatory enzymes, and total and specific mRNAs. For example, if a limiting protein L determines the transition from one time-compartment to another, then the expression of the mRNA for L could regulate that transition. Furthermore, the growth-rate $\mu$ can be represented as a linear function of the concentration of a given specific mRNA, and the rate of mRNA transcription can be represented as a non-linear function of the concentrations of two or more growth factors (or other regulators), or it can be assumed to be a combination of growth associated and stimulus-dependent kinetics. In turn, the steady state values of all enzyme synthesis rates and the total specific RNA level are a function (linear for RNA) of the steady-state specific growth-rate $\mu$. The total RNA can be used as a measure of the growth resources of the cells, since the ability to increase a stimulus-induced specific sRNA is limited by the amount of synthesis proteins, which in turn is limited by the amount of total RNA. Because the relatively high rate of RNA turnover and the dilution effect of cell growth, the [sRNA] responds immediately to a removal of the stimulus-effector. With an increase of the stimulus-effector, the rate of increase of [sRNA] is controlled by a time constant which is inversely proportional to the total RNA of the cell (Copella & Dhurjati 1990. Biotech. Bioeng. 35:356–374). With the system of this invention, the modeler would clone from the Palettes a set of bioReservoirs and bioProcesses of the appropriate types to represent the different terms of the following equations, which are then transferred to the appropriate compartments, connected and configured, and desired values are given to the model parameters. The following equations have to be adapted for use in the simulation formulas of the system of this invention.

$$(\mu=k_x*([mRNA]-[mRNA]o)\rightarrow(1/h)=(gX/gRNA)*(gRNA/gX/h);$$

$$\tau=k_x/(\mu+k_x*[mRNA]o/[X]),$$

where $k_x$ is the rate constant for mRNA transcription (gRNA/gX), $\tau$ is the time constant (gX/gRNA), and [mRNA]o/[X] is the specific [mRNA] at $\mu=0$. The growth rate can also be viewed as the sum of all rates in one simple anabolic pathway divided by the total mass (growth from glucose in bacteria): $\mu=(\Sigma r_i)/[X]$. The number of generations: $\Phi=\log(2)((X-Xo)/Xo))$ $$\mu G_1 * e^{\mu t} \int_\phi^\infty \lambda^{G1}(x)dx = G_1 * e^{\mu t}*([cc]^{G1}(\phi)*\lambda^{G1}(\phi)-r(G_1\rightarrow S)*\int_\phi^\infty \theta(x)dx),$$

where $\lambda^{G1}(x)$ and $\theta(x)$ are the frequency functions describing the cc content distribution for cells in $G_1$ and $G_1 \rightarrow S$ transition, respectively, and $r(G_1 \rightarrow S)$ is the rate constant that describe that transition;

$$r(G_1 \rightarrow S)=\mu/G_1*(N_0+G_2+S);$$

$$r(S \rightarrow G_2)=\mu/S*(N_0+G_2);$$

$$r(G_2 \rightarrow G_1)=\mu/G_2*N_0$$

The following equations are examples of how overall rates of synthesis can be used to implement black-boxes, where each of those equations provide the value for the Velocity of the black-boxes to be represented by the corresponding type of bioProcesses: for IFN-$\alpha \rightarrow$IL2: rs(TF-IFN-a)=k1 * [IFN-$\alpha$] and rs(mRNA-IL2)=k2 * [TF-IFN-$\alpha$] (or rs(mRNA-IL2)=1+ka [IFN-$\alpha$]/1+ka [IFN-$\alpha$]+ks;); rs(IL2)=k3 * [mRNAIL2].

By using the concentrations variables of sol-mol-pools, expressed as moles per volume units rather that per cell, it would not be necessary to adjust the steady-state concentration with growth for constitutive enzymes, since it is assumed that both increase at the same rate, while for regulated enzymes, the dilution effect is more apparent, since it is not paralleled by synthesis. In the current implementation focusing on regulatory processes, since most of them take place in the form of large molecular complexes, highly localized in some parts of the cell, it would be more meaningful to use the defined density variables (molecules per cell). To synchronize the simulation from the intracellular to the cellPool level, the quantities of all the bioPools of extracellular molecules are halved at each cell division transition. In addition, specific rates are rates per cell, and total rates are specific rates multiplied by the cell density. Specific cell components may increase throughout the cell cycle: a) continuously at a constant rate, b) at a rate that doubles when the DNA is replicated, c) at a progressively increasing rate which follows fist-order kinetics, or d) discontinuously, according to a sequence of events which changes the rates in a complex pattern.

When the mechanisms are unknown, a deterministic approach may be taken with the transitions modeled as a time-dependent events. As shown in FIG. 2, the cell-phase compartments, which are holders of mechanistic models, also have an attribute "interval" (217) to hold information about the experimentally observed duration of that phase of the cycle, which can be used during a simulation-run to deterministically deactivate such subworkspace when that period of time has elapsed since the subworkspace was activated, or whenever any type of known constraints are met. In the deterministic approach, the rate of the translocation process is defined by a rate constant, which may have a constant predefined value, or its value may be variable and set at run-time by a simulation formula, an expert rule, or procedure, such as one that reads the phase's "interval" just described, or it can be modeled by a model-block. The transfer of cells from cellPool i to cellPool j does not happen at once, but rather follows a Gaussian distribution, which may be modeled using the corresponding model-block.

Following is an example of a high-level representation of the effect of some drug on cell growth, when there is partial mechanistic knowledge available, but where most of the many other steps in the pathways leading from the external drug to the regulation of cell growth are unknown. In a system where enzyme $X_1$ produces a soluble substance c which is used in the formation of active enzyme $X_2$. If $X_1$ and $X_2$ represent the total amounts of $X_1$ and $X_2$ contained in n cells, and if $X_2$ is the component which, upon reaching a threshold, determines the occurrence of cell division, so that $n=\beta X_2$, where $\beta$ is a constant, then, assuming steady-state, when c remains at a steady concentration and therefore the formation of $X_2$ is proportional to $[X_1]$), follows that: $d[c]/dt=A(X_1/n)-B(X_2/n)[c]-C[c]=0$, (1) where A, B, and C are constants. From (1) it can be said that $c=\beta X_1/X_2$, and following a set of derivations it results that the growth rate is: $k=d(\ln n)/dt=d(\ln X_2)/dt$. If now c decreases from the action of some drug, then $X_2$ which is proportional to $[c]$ decreases. The cell growth rate $dn/dt=\beta dX_2/dt$ will also decrease. The effect of the drop in c is an increase in $X_1$ relative to $X_2$, until a new level of $X_1$ is reached that restores the cell growth rate to its initial value. In the representation used in the current embodiment of this invention:

- the 1st term is represented by an enzyme-bioProcess corresponding to the formation of c by $X_1$, where the enzyme-bioReactant would be connected to the bioPool of $X_1$, the substrate-bioReactant would be connected to the bioPool of the precursor of c, and the bioProduct would be connected to the bioPool of c;
- the 2nd term is represented by an complex-formation-bioProcess corresponding to the consumption of c in the formation of $X_2$ from c and other subunit(s), connected to the appropriate bioReservoirs; and
- the 3rd term could be represented, depending on the specific biologic mechanism to be modeled, by: a) a complex-formation-bioProcess corresponding to the consumption of c in the formation of a complex leading to the loss of c by degradation by a ubiquitin-dependent mechanism, connected to the appropriate bioReservoirs; or b) a translocation-bioProcess, representing other mechanisms of loss of c, such as by diffusion, connected to the appropriate bioReservoirs; or c) implicitly represented by the degradation-coeff within the formula that determines the current amount of c, which includes a term with default degradation.
- in this system, the scaled-amount set of variables is used, because what is relevant for the behavior of the system are the relative value of $X_2$ in relation to its threshold, which determines cell division, and the ratio between $X_1/X_2$, which regulates the rate of production of $X_2$, and not their absolute amounts.
- the value of the number-of-cells attribute of the cell-bioModel that contain those bioProcesses and their corresponding bioReservoirs, is doubled when the scaled-amount of the bioPool of $X_2$ reaches the threshold, and at the same time, $X_1$, $X_2$ are halved while [c] remains constant.

The above example is an oversimplification, and in fact much more is currently known about the mechanisms that determine the initiation of mitosis, in which complex interdependencies are involved, such as the equivalent of $X_2$, a complex, regulating not only the rapid increase in its production by a positive feedback loop upon the equivalent of $X_1$, but also $X_2$ regulating its destruction by activating an enzyme in the ubiquitin-dependent mechanism, and $X_2$ regulating its inactivation by activating another enzyme that converts $X_1$ back to c. In general, in the absence of diffusion, the simple case that might produce organization in time is that of two concentration variables, $X_1$ and $X_1$, where the value of each is dependent on the value of both, such as when: $d[X_1]/dt=v_1$ $(X_1,X_2)$; and $d[X_2]/dt=v_2$ $(X_1,X_2)$.

Other high-level physiological events can be modeled in a similar manner, such as considering different cells subsets (i.e. neutrophils) changing compartments (intravascular→interstitial space during inflammation) as induced by cytokines (i.e. TNF-α, which is produced upon activation by macrophages, neutrophils, T-lymphocytes, natural killer cells and mast cells), in chemotactic-bioProcesses. The time-period that a cell subset stays in such a compartment depends in part on the expression of adhesion proteins (such as E-selectin (ELAM-1) or ICAM-1 by endothelial cells, which expression is induced by TNF-α, that will be components of cell-interaction-bioProcesses. Other examples are shown in FIG. 12 for processes representing secretion (1202), cell activation (1205), cell-differentiation (1209), cell-interaction (1211), and cell dissociation (1223);

3. Modeling Progression through Different Cell States: The Cell Cycle and Cell Differentiation Each cell-phase has two attributes called the Generation-number (Φ,218) and the Number-of-cells (N, per volume unit 219). At each cell division at the mechanistic level, that is, when the subworkspace of the M-phase compartment (206) is deactivated and optionally the subworkspace of the G1-phase compartment (203) is activated, predefined expert rules set Φ=Φ +1 and N=2n for each cell-phase of that cell-bioModel. Another attributes called Mass-per-cell (X), can optionally be given a value and used to calculate specific values as a function of cell mass, in which case predefined expert rules (Table 40) set X=X/2 for the G0-phase (202), and the G1-phase (205) if applicable, of that cell-bioModel, and then the value of that attribute would be modeled as dependent on time or as dependent on any other variable(s), such as the concentration of some specific mRNA(s) or protein(s), until reaching again a value of X or close to X. In turn, the value of X can be used to adjust other quantities or to control the activation and deactivation of the subworkspaces of each successive cell-phase of that cell-bioModel, making it dependent on cell-size. The equivalent at the population level at mitosis is that n cells from the M-phase bioPool are translocated to the G0-phase (or the G1-phase depending on the situation) bioPool while multiplied by 2, so that the G0(G1)-phase bioPool receives 2n cells.

Figure 13:
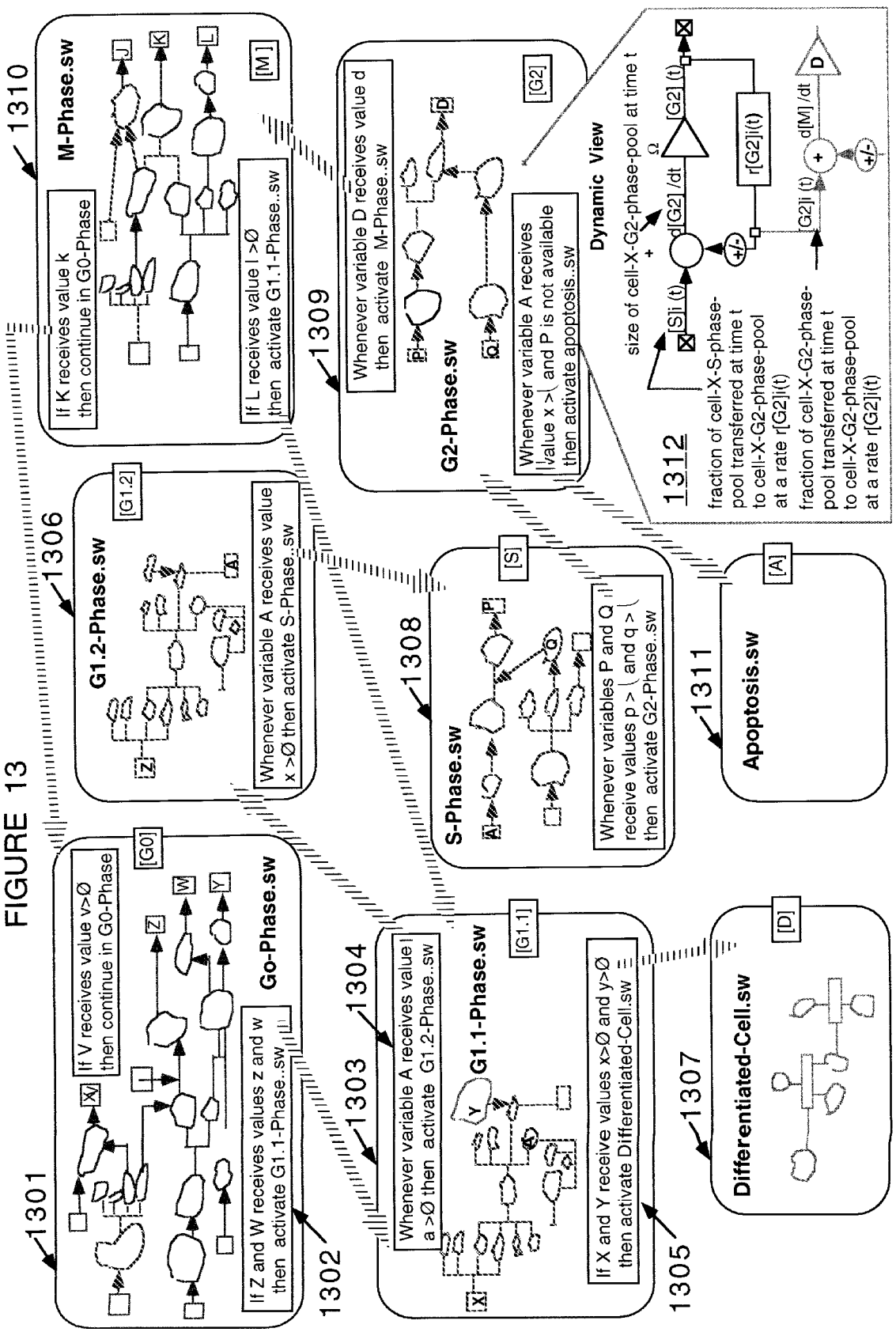
FIG. 13 is an schematic representation of the combination of the inference and simulation capabilities used in this invention to simulate iconic compartmentalized model of complex systems.

FIG. 13 is a representation of the mechanistic approach, and attempts to represent on paper what can be achieved dynamically at run-time applying the innovations of this invention. If we assume that a cell is in G0-phase state and focus on that state's sub-workspace (1301), and there we assume that variables represented as Z and W have received the values z and w, respectively, then following the implementation described in this invention, a rule will be invoked (1302) that will activate the subworkspace of the G1.1-phase (1303) compartment. Activation of G1.1-phase.sw implies that all the variables and parameters encapsulated within the bioObjects contained upon that subworkspace will be available to the simulator, and the data flow can now continue through any branch of the pathways represented there. Therefore, upon required events being satisfied, such as Z and W reaching certain thresholds-which could be an effect of binding one or more growth factors to their receptors on the cell membrane-, the cell makes a transition from the G0 to the G1.1 phase. The subworkspace of the G0-phase remains activated during the whole simulation run because it contains all those bioProcesses that are not cell cycle specific. Focusing now on the simulation of the G1.1-phase (1303), two expert rules could be invoked, saying that "Whenever variable A receives a value a>φ1 then activate G1.2-phase.sw" (1304), or "If X and Y receive values x>φ2 and y>φ3 then activate Differentiated-Cell.sw" (1305) and depending on which one is invoked first, either the subworkspace of the G1.2-phase (1306) compartment or the subworkspace of the Differentiated-Cell.sw (1307) compartment will be activated, since the subworkspace of the G1.1-phase (1306) compartment will be deactivated by another two expert rules that state that "Whenever the subworkspace of the G1.2-phase (or Differentiated-Cell) is activated then deactivate the subworkspace of the G1.1-phase". This way of reasoning apply to the other cell-phases as well, with the difference that the options vary for each cell-phase. For example, the G1.2-phase (1306) and S-phase (1308) may be committed to only one option, with the time for progression to the next phase being determined by one rule, as shown, while the G2-phase (1309) and M-phase (1310) have two options, and which one will be activated is controlled by two rules, as described above. One of the options, Apoptosis (1311) is a dead-end stage, representing regulated cell death. While in M-phase (1310), a live cell's program tells it, before or during cell division, to continue proliferating, in which case one or both the daughter cells entering again the G1.1-phase, by activating the subworkspace of the G1.1-phase, or to exit the cell-cycle, in which case the simulation continues with only the Go-phase. Note that the options for each one of the cell-phases have been predefined by the characteristic number of stubs for each subclass.

The dynamics system diagram (1312) in that figure is used to represent that the defined attributes of the subclasses of cell-phase contain a variable that allows to keep track of the proportion of the cells (220), from the original number on Go-phase, are progressing through the phases of the cycle, as an alternative to build a model with a set of bioReservoirs and bioProcesses. This variable can be modeled using a probabilistic or mechanistic approach. In a probabilistic approach for representing cell-phase distributions, a balanced growth type of cell population is characterized by such distributions, which is a time invariant property even if their total number increase exponentially with a constant specific growth rate $\mu$. Each of the subsets of that population, which represent different cell-phases, and which can also be represented as separate cellPools in the system of this invention, increase in number at the same specific rate and are also characterized by time invariant property distributions, which is represented by the "typical-fraction" attribute of each of the cell-phases. At some steps during a simulation, the alternative cell-phase compartments that could follow may exclude each other at the single cell level, but not at the cell population level, so that different subsets of a population may follow different paths, with the distribution depending on the strength of signaling events generated within the simulation itself. Therefore, the simulation of the value of this variable could be modeled to represent the probabilistic distributions, independently of which subworkspaces are activated first following the mechanistic approach.

As shown in FIGS. 3 and 14, If a cellular response results only in proliferation, the simulation of the population cell dynamics involving bioPools of cells in different states, results in cells that keep translocating from bioPool to bioPool (304, 306, 309, 311, 313, 316), each representing a different one from a discrete number of states, resulting in cycles through a closed-loop set (301) of cell-state bioPools, one of those shown on the top half of FIG. 14. However, if the response results in cellular differentiation, it generates branching (307, 412, 414) to a new closed-loop set (302) of cell-state-pools.

FIG. 14 shows how a cell populations approach bioModel can be build to model the translocation of cells between the major states considered, as mechanistically represented by the defined subclasses of cell-phase, by creating and connecting a set of bioReservoirs and bioProcesses, as the example detailed in the figure shows. Although the cell cycle is a continuous one, it can be compartmentalized into functional cycle intervals whenever it is deemed useful to better represent the dynamic simulation of the system. The initial state is the resting state, represented by the cellPool Cell-X1-Go (1401), which contains cells of type X1 (or in differentiation stage X1) in the Go-phase. That cellPool may receive inputs (1402) from various sources, represented by bioProcesses in which cells are added to the resting pool after having been activated or cycling as the result of a variety of factors, and its outputs (1403) may contribute also to a variety of such bioProcesses, such as the one that will be here described. While at Go-phase, if the cell are activated (1404) by a growth factor (1405), antigen or any other activating stimulus, the cells enter the activated state or G1.1-phase (1406) and are added to the corresponding bioPool (1411). From that bioPool (307, 412), all the cells may follow one of the two different options, or different cells may follow different options for the next cell-phase, depending on the type and strength of the signals received, either: a) following the cell cycle (308, 1408) if certain growth factor(s) (1409) are sufficiently present, resulting in cells X1 in G1.2-phase (1410) and added to their corresponding bioPool (309), or b) following the cell differentiation pathway (307, 1412) if certain differentiation factor(s) (1413) are sufficiently present, resulting in cells X2 in G1.1-phase (1414) and added to their corresponding bioPool (1415), and these cells will now follow a new set of cell masses (302). Each of the cell types will be then running in parallel (301, 303) with their own set of bioReservoirs and bioProcesses. The same reasoning applies to the rest of the system, as detailed in the figure, which will not be further explained, only to say that at the end of the cell cycle, in the cellEngine (1416) that returns cells from M-phase (1417) to G0-phase (1418), has not only a translocation function, but in addition, given that the "stoichiometric-coeff" of cell-X1-Go is 2 while the "stoichiometric-coeff" of cell-X1-M is 1, it doubles the number of cells to be added to the cell-X1-Go-pool.

In fast growing organisms, the dilution factor resulting from cell growth is represented by $\mu$, while in slow growing cells direct enzyme degradation is more important, since the levels of many enzymes in animal cells is controlled by the balance between enzyme synthesis and degradation, called turnover. The synthesis of an enzyme is a zero-order process, while the degradation usually has a first-order kinetics (proportional to the concentration of enzymes).

It is very difficult to measure directly the rates of change of different cellular components at the single cell level. A modeling framework requires at least data from measurements about the distributions of single-cell components in growing cell populations, and at the time of cell division and birth, which in some cases can be obtained by multiparameter flow cytometry.

Growth rate in terms of net rate of protein accumulation in single cells in each phase of the cell cycle.

The growth rate in terms of net rate of protein accumulation in single cells in each phase of the cell cycle can be calculated, for balanced growth cell-populations, based on the measured distributions of single-cell protein content in the total cell population. Similarly, net rates of accumulation of any specific protein as well as any other compound or property can be calculated whenever the properties and their distributions can be measured on a single cell basis, such as with multiparameter flow cytometry with gating features, that permit direct correlation with the cell-cycle phase. Kromenaker and Srienc (1991) defined balanced growth-cell populations as those characterized by: a) the total cell number increasing exponentially with time according to a specific constant mean growth rate, and b) the total cell population and any of its sub-populations having a time invariant single-cell property distributions. They developed equations to represent the dynamics of a given protein content range in an individual cell cycle, and after deriving restrictions that apply to the rate constants and substituting those in the original equations, the obtained expressions for the growth rates for each individual cell cycle. The transformation of this model into the graphic language proposed in this invention, and the incorporation of those equations, is an example of a currently preferred embodiment of this invention.

The transition between different time-compartments may also be made a function of cell size, or its equivalent total-protein content, both of which are attributes of cell-bioModel. At the population level, the transfer of cell-units from the bioPool of cells in G1.1-phase to the bioPool of cells in G1.2-phase is also based on the value of such attributes. For example: the rate of increase in the number of cells with a protein content greater than a given value p in G1, which may be established to delimit the G1.1-phase from the G1.2-phase compartments, equals the rate at which cells with a protein content greater than p enter G1-phase+ the rate at which cells within G1-phase grow into the class of cells with a protein content greater than p–the rate at which cells with a protein content greater than p exit the G1-phase.

Additional sub-phases can be analyzed whenever appropriate landmarks can be observed to define additional transitions. To represent a specific form of cell death, which is highly regulated and known as programmed cell death or apoptosis, a separate time-compartment is defined in this system, which is equivalent to a cell-cycle phase compartment but with the difference that has a dead end and does lead to a next compartment, but rather eliminates cells that have passed through certain specific combination of events. In addition, an additional term representing the rate of exit from each cell-cycle compartment via other types of cell death may be introduced into each of the population balance equations.

In this system, in general it is assumed that cell division is symmetric, and that total protein is conserved at cell division. The G1-phase is bounded by cell birth and initiation of DNA replication; S-phase is bounded by the initiation and completion of DNA; G2-phase is bounded by the completion of DNA synthesis and the initiation of mitosis; and the M-phase is bounded by the initiation of mitosis and cell division. At balanced growth, each subset of cells in each cell cycle phase increase in numbers at the same specific growth rate as the overall population. The rate of entry into the G1 phase is twice the rate of exit from the M phase.

Additional phase compartments can be added whenever other transition landmarks can be measured, as well as the cell distribution at each side of the transition. The following can be used as the equations to model the rates: $rG2G1 = k * No/G20$, $rG1S = k * (No+G20+S0)/G10$, $rSG2 = k * (No+G20)/S0$, where No is the number of cell in the total population at some reference time, and $No = G10+G20+S0$ at this time.

The currently preferred embodiment of this invention deals with different stages of cell differentiation, each representative of a characteristic set of behaviors, as separate pools of cells. All the cells in a pool have identical behavior and, again, in the system of this invention when one refers to an instance of a cell with a particular phenotype it does not mean an individual cell but rather a pool of equal cells that is characterized by its behavior and also by a cell-number and a cell-density. We have also considered previously cases where individual cells grow and differentiate in response to specific signals provided when environmental factors activate specific receptors that initiate a signal transduction pathway within the cell. However, different cells respond by following diverse pathways in response to an identical signal, and this specific response depends on the history of that cell. For example, erythroid cells could be allotted to three pools with phenotypes characterized by the presence of two cell differentiation surface markers CD34 (a glycoprotein) and CD71 (the transterrin receptor): a) $CD34^+$ include most immature erythroid progenitor cells; b) $CD71^{low}$ includes intermediate stages; and c) $CD34^- CD71^{high}$ includes most mature erythroid progenitors. Each of this populations have different predominant form of the erytropoietin receptor, and respond in different ways to erytropoietin: $CD34^+$ express a truncated form of the receptor and respond by proliferation, while $CD34^- CD71^{high}$ respond by differentiation and are protected from apoptosis or programmed cell death (Nakamura et al., Science 257, 1138–1141, 1992). In the currently preferred embodiment of this invention, the particular history of each cell pool is reflected in the specific bioModels as determined by the particular procedures to be followed, which are encoded in the corresponding attributes of the bioObjects that are components of that cell's specific bioModels.

F. GENERAL AND NAVIGATION MODE: Newly Defined Query and Constrained Navigation Capabilities 1. Initialization The following description of the initialization procedures, as well as the simulation procedures and other complex processing described later, are meant to only highlight the major tasks accomplished accomplished by those procedures that been modified or added. This is not meant to substitute for the more detailed descriptions provided in the pseudo-code listings provided in the form of tables in the Appendix, as referred to within this text section, in addition to the detailed description and Appendix of the accompanying patent filing with Ser. No. 08/373,992, where the major body of the processing is described, and where the current procedures are either modifications or expansions.

The navig-init-proc has been modified to additionally call, for each bioModel in the application, the bm-initialization-proc (Table 60), which scans each bioModel for other contained bioModels, bioProcesses and bioReservoirs, going down the subworkspace hierarchy, and establishes the following relations between any combination of them: bm-contained-in between a bioModel and a bioModel, bp-contained-in between a bioProcess and a bioModel, and br-contained-in between a bioReservoir and a bioModel (Table 61). Those relations are important for all further processing, and are used by the newly defined query procedures, navigation procedures, and simulation procedures described below. A rule (Table 62) monitors the application at run time, and whenever the user moves a bioModel the rule starts the biomodel-ws-check-proc, which checks whether the bioModel has been moved to a different workspace, in which case it calls the remove-biomodel-containing-proc (Table 62), to brake the old relations that no longer apply, and calls this bm-initialization-proc (Table 60) to establish the new relations.

2. Query Mechanisms

Figure 15:
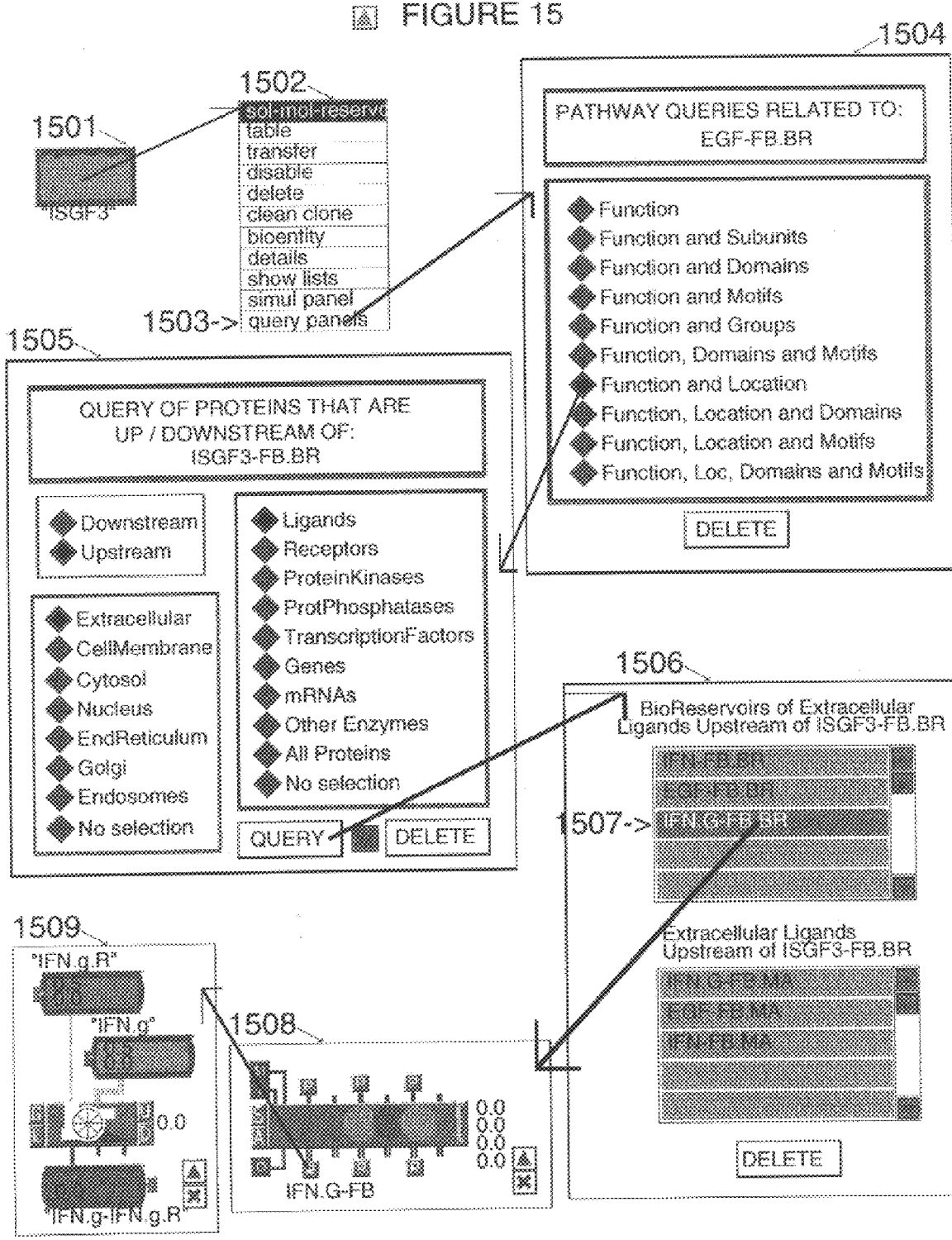
FIG. 15 describes an example of the predefined Query Panels and their use.

As shown in FIG. 15, a BR-Query may be requested, as in the system described in the accompanying filing with Ser. No. 08/373,992, from a bioReservoir (1501) by selecting from its menu (1502) the "query panels" option (1503); or b) from the subworkspace a bioReservoir by selecting the query-tracer (not shown), which starts the create-br-related-selection-panel-callback (not shown), which creates a clone of Master-BR-Molecular-Query-Panel, configures it, and displays its subworkspace (1504). The difference in this application is that the last four options have been added to that Panel, to include several of the queries previously defined in combination with a newly defined constraint criteria, the location of those bioReservoirs previously selected by the other criteria within the different cell compartments (Table 63). Selection of any of those new options, displays one of the newly defined Query Panels (1505). In this new set of Panels, the "Downstream" and "Upstream" radio buttons are associated instead with the downstream-function-location-callback and upstream-function-location-callback (Table 64), respectively, which call the downstream-location-query-lists-proc (Table 65) or its upstream equivalent (Table 66). Those procedures in turn call some of the procedures described in the accompanying filing, and also call a newly define procedure, find-compartment-proc (Table 67). The user may additionally selected any combination of one radio-button each from the radio-boxes offered in that particular panel, which in the example shown include only the "location" box (1510) and the "function" box (1511), but which in other panels may include also one or two of the alternative types of "structure" boxes. After the selection is done and the previous processing is completed, selection of the "Query" button by the user calls the query-br-related-location-callback (Table 68), which in turn, depending on the boxes available on the particular Panel, calls one of an alternative set of procedures, which in turn call other procedures. The reader is referred to the listings in Tables 69 through 81 for the details of that very complex processing which is difficult to describe, but which use a similar approach and methods are used to create a new set of lists and to merge lists with bioReservoirs meeting the different criteria, as those described in the accompanying filing. The output of such query based on the user selections is graphically displayed (1506) in a format that allows further selection of any of the bioReservoirs (1507) resulting from that search to directly access the details of the bioReservoir itself (1508), which then allow to continue navigation to all connected bioProcesses (1509), or to perform any of the capabilities otherwise available in General Mode. The bioEntities resulting from the combined structural searches, if any, are also listed in the lower half of the panel (1512). These displays are not different from those described in the accompanying filing, other than a more complex text is generated to include the additional criteria.

Figure 16:
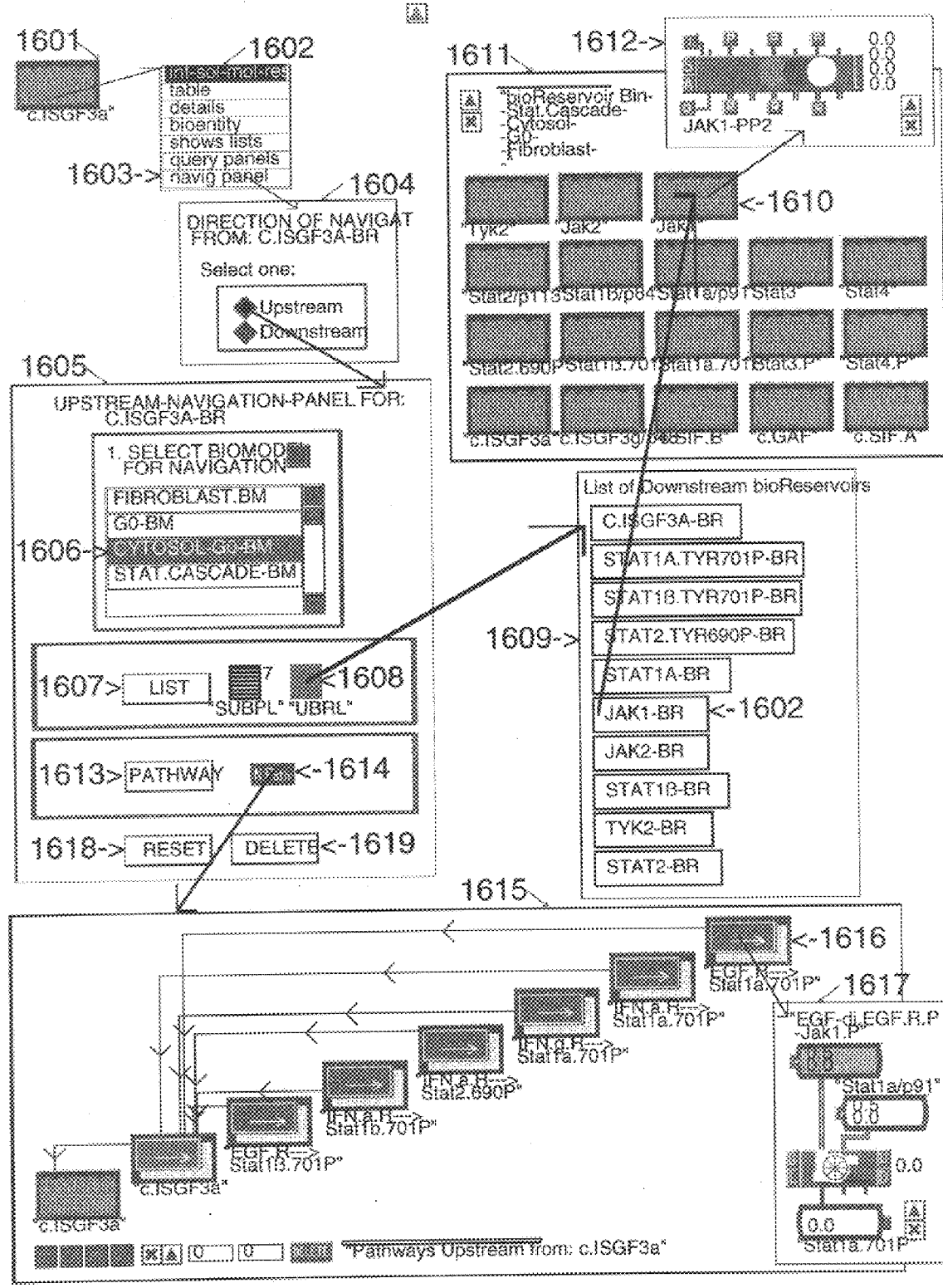
FIG. 16 describes an example of the predefined Navigation Panels that a user can request from any reservoir within the iconic compartmentalized model for the dynamic generation of constrained pathways of all the processes that are either upstream or downstream from that reservoir, but which are contained within a compartment selected by the user.

As shown in FIG. 16, a new graphical Interface , the Navigation Panel (1605), and associated methods have been also added to this application, which will be briefly below by comparison with the Simulation Panel.

The underlaying shell loads the desired application modules on memory for run time operations, but it is able to merge and remove modules while the system is running. Since the inference engine's reasoning and search space is limited to those modules that are loaded, it is necessary to create a mechanism to allow for searches in modules that are not yet loaded on memory. This is accomplished by maintaining in the repository module an object, called the query-arrays-bin, which holds in its subworkspace a set of item-arrays for intelligent dynamic merging and removal of the modules required at particular times, particularly when searching through the bioEntity-module and In order to allow for searches in a modularized application. Those contained-in-module arrays are built following similar methods as those described here for bioModels. The difference is that a new set of relation is defined, of the series -contained-in-module, and an initialization procedure that loops over all the workspaces of each loaded module, finding out the value of their assigned-module, and then looping over all the bioModel Libraries upon each workspace, and over all the bioModels upon each bioModel Library, and the continuing with the methods described in the previous section.

G. SIMULATION MODE: Expanded and Alternative Simulation Interface and Methods

Figure 17:
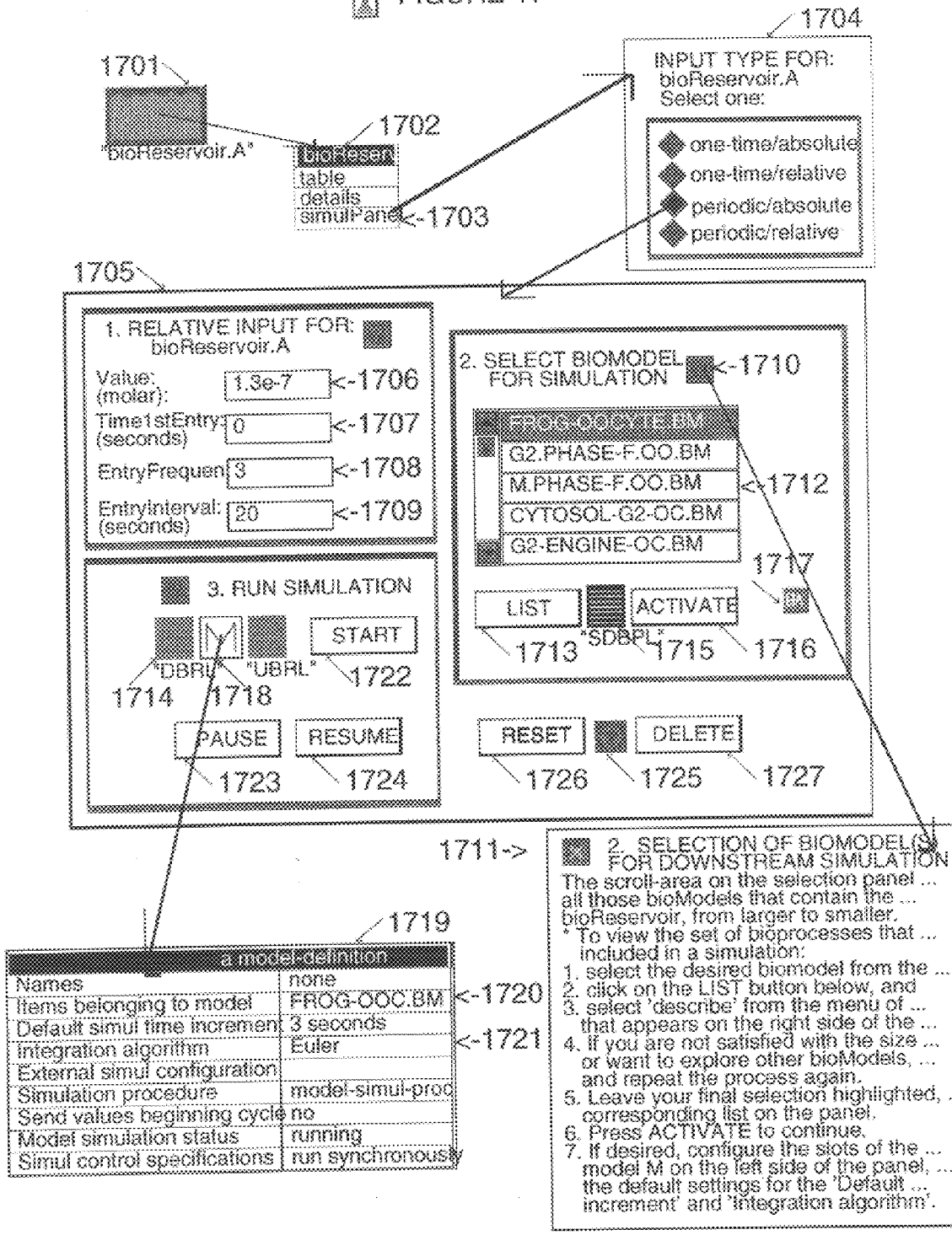
FIG. 17 describes an example of the predefined Simulation Panels that the user can request from any reservoir within the iconic compartmentalized model the dynamic generation of constrained pathways and for the control of the dynamic simulation of the kinetics of those pathways.

1. As shown in FIG. 17, the Simulation Panel (1705) used as the graphical interface to start (1700) and control (1723, 1724) quantitative simulations, described in the accompanying filing with Ser. No. 08/373,992, has been expanded to deal with the larger compartmentalized bioModels that are an innovation of the current application. A new structure has been added (1712) to the interface that is dynamically created, together with the Panel, and which reference point is the bioReservoir from which the Panel was requested. That scroll lists any bioModel that contains such bioReservoir, at any level in the hierarchy, to allow selection of an adequate size of the model to be simulated. The instructions on how to use that part of the panel are shown (1711). Note that the user does not need with this implementation to transfer the submodel to the Panel, and now the "items-belonging-to-this-model" (1720) now names the bioModel selected by the user, but it is set by the program. This is particularly important when dealing with very large systems, allowing to focus the computer resources on the subsystems of interest. Other required modifications are those to include reference to the new subclasses of bioObjects defined in the current application. All the procedures that have been modified or added to those procedures described in the accompanying filing, are listed in Table 101 through 111. In addition, another alternative implementation of these simulation procedures has been developed to allow to perform simulations, and further navigations, with copies of the original bioProcesses and bioReservoirs, so that the values of the originals are not modified. This allows various users to access the same copy of the application from several windows, simultaneously with one or more of those users performing simulations when operating in Simulation Mode. The modified procedures for this alternative implementation are listed in Table 112 through 123.

2. As shown in FIG. 16, a new graphical Interface (1605) and associated methods have been also added to this application, which uses the same new scroll structure (1606) to select bioModels and to generate lists. However, the purpose of this interface, called a Navigation Panel (1605), in addition to the navigation (1609–1612) that can be initiated from the elements (1602) of the generated lists (1608), is the creation of upstream (1615) or downstream pathways that are now constrained to the bioModel selected by the user. The procedures associated with this Panel are listed in Table 82 through 100. This panel is not to be used in General Mode, and therefore not available in Simulation Mode, since these procedure do not activate the subworkspaces of the selected structures, as those associated with the Simulation Mode do.

Figure 18:
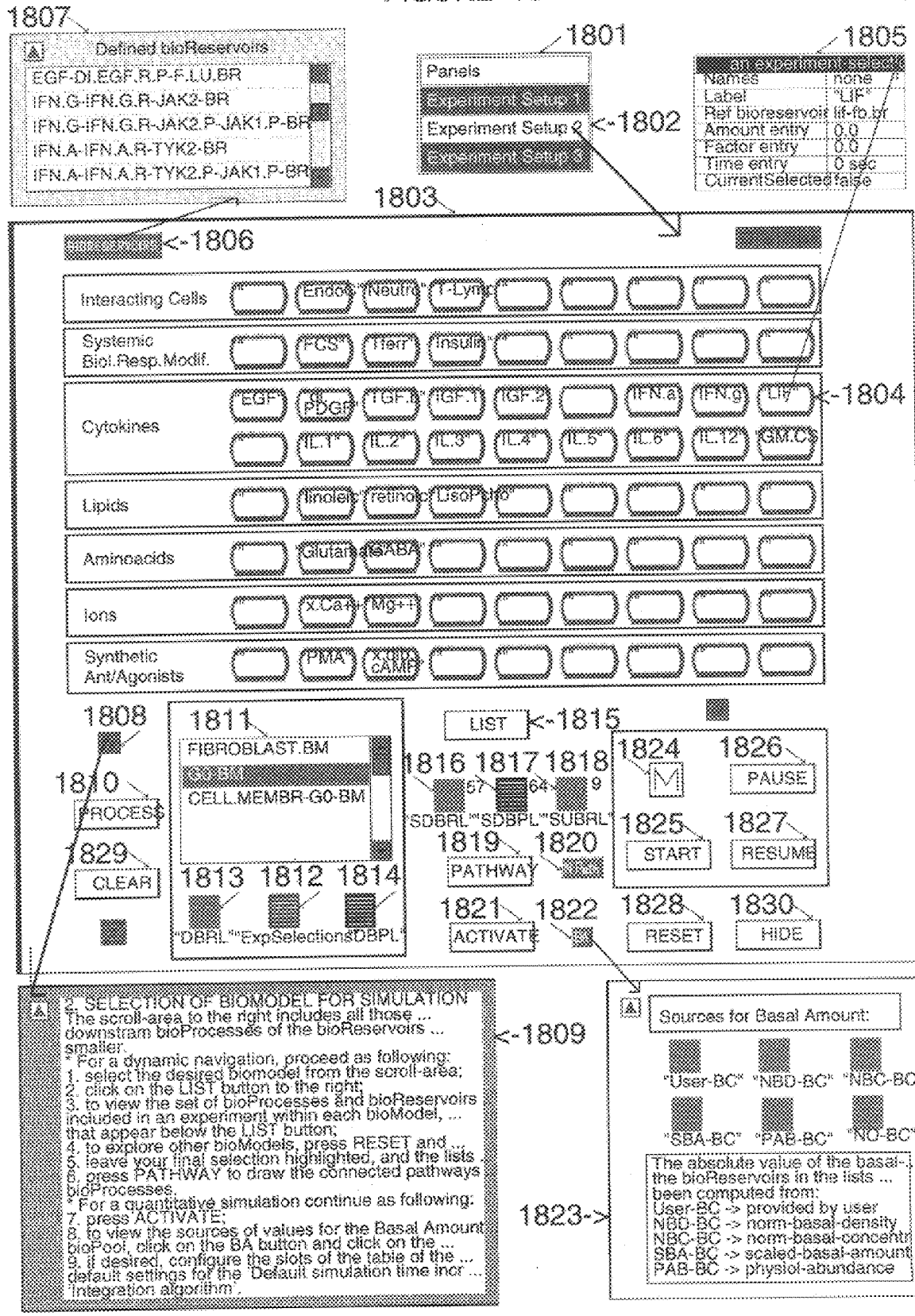
FIG. 18 describes an example of the predefined Experiment Panels that a user can select from the domain menus to request the dynamic generation of constrained pathways from multiple initial points and for the control of the dynamic simulation of the kinetics of those pathways.

3. As shown in FIG. 18, the same scrolling structure (1811) has been added to the the Experiment Panel (1803) interface, and what was said above applies here in a similar way, with the different that the search for the containing bioModels may apply to more that one bioReservoir. The procedures associated with this Panel that are modified or added to the procedures described in the accompanying filing with Ser. No. 08/373,992, are listed in Table 124 through 126.

4. Some of the initialization procedures have been modified or added as well, to initialize the newly defined classes of structures, and to established the contained relations, which are listed in Table 59 through 62.

5. This system's graphic interface allows simulations to be followed in different ways, including:

creating pathways on a workspace where dummy copies of the bioProcesses involved, or full copies of both the bioReservoirs and bioProcesses involved (depending on the alternative method of simulation used) of all the participating), are located in sequence and the corresponding connections between them are drawn. This structures allow to further interactively navigate through the system as usual, including back to the originals from which the copies were made.

animation by color changes of the activated parts of the schematics;

display of the current values of desired variables in digital form (1612, 1617);

dynamically created graphs of a set of time series of the values of desired variables; and dynamic charts of the values of a variable versus another variable;

6. A simulation starts with the baseline model, after being initialized by setting the initial values of the initial amounts of the bioPools (concentrations, densities, scaled-amounts, or other quantities, depending on how the bioPools involved where defined) to be equal to the values of the corresponding basal amounts. In order to activate the system, a disturbance may be introduced by entering one or more input values through the entry-panel of the desired bioReservoir, or through the tables (1805) of the desired experiment-selections (1804) of the experiment-panel (1706, 1709). By entering different values for those variables, or by changing the values of the constant parameters, what-if analysis can be performed on the system. Montecarlo simulations can be performed using a montecarlo-model-block as an input to each of the bioPools desired as test inputs, as explained in other section, and the simulation can then be started from either the entry-panel of a desired bioReservoir, or through the desired experiment-selections of the experiment-panel, without entering entry-values. The history of values for each of the variables of interest can be stored in the form of a matrix-like structure that is an array of arrays of values for each variable or parameter. The values of those arrays are transient values that can be used for statistical and sensitivity analysis within this system, or can be archived to a text file external to the system of this invention, or the values can be transferred to an external statistical package for further analysis. In addition, if the values of those arrays are desired in a permanent form within this system, this is accomplished by using the procedure provided to make the initial values of an array equal to the list of its current values, separated by commas.

What is claimed is:

1. A computer-based system for creating hierarchical virtual-models of dynamic complex-systems, comprising:

libraries of prototypes of building-blocks representing different types of components characteristic of said complex-systems, instances of said prototypes being used to represent components of the complex-system to be modeled, wherein:

certain of said prototypes are simple building-blocks;

certain of said prototypes are composite building-blocks for representing different levels of organizational complexity, each comprising or enabled to comprise any number of instances of building-blocks representing its components;

said simple or composite building-blocks are to be organized within instances of said composite building-blocks in a hierarchy of any number of layers representing organizational compartments or subsystems modeled at different levels of abstraction;

said building-blocks may comprise any number of attributes with values of any type, including but not limited to: character string, integer or real numbers, logical values, fuzzy values, or instances of images, parameters, variables, lists, arrays, or any other object or data structure, or pointers to instances of any of said building-blocks, external files, Uniform Resource Locators (URLs), database records, or any other objects, in said computer system or in a network accessible by said computer system;

program means for manipulating selected instances of said building-blocks comprising:

means to make said prototypes of building-blocks avalaible, including visual means through menus or palettes and/or programmatic means;

means to instantiate said prototypes of building-blocks, including constructor means to create new instances from their definitions and/or means to clone semi-configured instances of said prototypes of building-blocks, interactively and/or programmatically;

means for establishing links between interrelated instances of said building-blocks, directly or through their components; and means for displaying the components of said composite building-blocks and/or the building-blocks at the other end of said links.

2. A computer-based system as claimed in claim 1, wherein said libraries comprise one or more prototypes of composite time-compartment building-blocks, which instances are used to represent discrete physical or conceptual time intervals characteristic of said complex-systems, each instance capable of holding any number of instances of said building-blocks, including other instances of time-compartment building-blocks, without any limits as to how many layers of lower-level time-compartment building-blocks are built-in to best partition said complex-system into a hierarchy of subsystems.

3. A computer-based system as claimed in claim 2, wherein:

said libraries comprise one or more different prototypes of process building-blocks comprising one or more inputs and/or outputs, each instance of said prototypes to be used to represent a process of said complex-systems with its input(s) and/or output(s), different prototypes representing different types of processes characteristic of said complex-systems;

said instances of process building-blocks of said virtual-models are to be organized within instances of time-compartments of said hierarchy; and said linking means allow establishing directional links between any of said outputs and inputs of any number of other instances of building-blocks.

4. A computer-based system as claimed in claim 3 further enabling modeling the dynamic quantitative behavior of said virtual-models or their subsystems, further comprising:

one or more different types of quantitative variables associated with corresponding prototypes of building blocks and/or their components, representing characteristics of the components of said complex-systems they represent; and methods associated with each of said types of variables to dynamically compute the values of instances of said variables comprised in a model during a simulation run.

5. A computer-based system as claimed in claim 2, wherein:

said libraries comprise one or more prototypes of reservoir building-blocks comprising at least one input or one output, each instance of said prototypes to be used to represent a population of any number of units of entities of one given type, or in one given state or compartment, with its input(s) and/or output(s), and wherein each of said population does not need to be physically separated, in a reservoir or otherwise, from other populations of entities in said complex-systems; and said instances of reservoir building-blocks of said virtual-models are to be organized within said instances of composite building blocks representing an organizational-compartment hierarchy; and said linking means allow establishing directional links between any of said outputs and inputs of any number of other instances of building-blocks.

6. A computer-based system as claimed in claim 5 further enabling modeling the dynamic quantitative behavior of said virtual-models or their subsystems, further comprising:

one or more different types of quantitative variables associated with said prototypes of reservoir building-blocks and/or their components, and simulation means, including methods associated with each of said types of variables to dynamically compute the values of any instance of said variables of any instance of corresponding building-block comprised in a model during a simulation run, said values being dependent on the values of any number of variables of other building-blocks linked to input(s) of said instance of building-block.

7. A computer-based system as claimed in claim 5, wherein:

said libraries comprise different prototypes of entity building-blocks, simple or composite, representing different types of entities or entity-components characteristic of said complex-systems, wherein instances of said entity building-blocks are to represent a description of the composition, modular structure, or other characteristics of a representative unit of any of the types of entities that participate in said processes;

said reservoir building-blocks comprise means for any instance to reference the corresponding instance(s) of said entity building-blocks; and said means further comprise means defined for said reservoir building-blocks to display said referenced instances of entity building-blocks.

8. A computer-based system as claimed in claim 2, wherein:

said libraries comprise one or more prototypes of reservoir building-blocks comprising at least one input or one output, each instance of said reservoir building-blocks to be used to represent a population of any number of units of entities of one given type, or in one given state or compartment, with its input(s) and/or output(s), and wherein each of said populations does not need to be physically separated, in a reservoir or otherwise, from other populations of entities in said complex-systems; and said instances of reservoir building-blocks of said virtual-models are to be organized within instances of time-compartments of said hierarchy; and said linking means allow establishing directional links between any of said outputs and inputs of any number of other instances of building-blocks.

9. A computer-based system as claimed in claim 8 further enabling modeling the dynamic quantitative behavior of said virtual-models or their subsystems, further comprising one or more different types of quantitative variables associated with corresponding prototypes of building-blocks and/or their components representing characteristics of the components of said complex-systems they represent; and methods associated each of said types of variables to dynamically compute the values of instances of said variables comprised in a model during a simulation run.

10. A computer-based system as claimed in claim 1, wherein:

said libraries comprise one or more different prototypes of process building-blocks comprising one or more inputs and/or outputs, each instance of said prototypes to be used to represent a process of said complex-systems with its input(s) and output(s), different prototypes representing different types of processes characteristic of said complex-systems;

said instances of process building-blocks of said virtual-models are to be organized within said instances of composite building blocks representing an organizational compartment hierarchy; and said linking means allow establishing directional links between any of said outputs and inputs of any number of other instances of building-blocks.

11. A computer-based system as claimed in claim 10, wherein:

said prototypes of process building-blocks are composite, said inputs and outputs being visual components comprising one or more instances of one or more types of reactant building-blocks representing the one or more inputs to said process as well as the one or more different roles played by said one or more inputs in said process, and one or more instances of product building-blocks representing the one or more outputs from said process; and said linking means allow to establish links between any of said instances of product building-blocks and reactant building-blocks of any number of said instances of process building-blocks, wherein each instance of reactant building-block may be linked to products of any number of said instances of process building-blocks.

12. A computer-based system as claimed in claim 10, wherein:
said libraries comprise one or more prototypes of reservoir building-blocks comprising at least one input or one output, each instance of said reservoir building-blocks to be used to represent a population of any number of units of entities of one given type, or in one given state or compartment, with its input(s) and/or output(s), wherein each of said inputs and outputs of said process building blocks are to be linked instead to any number of output(s) or input(s), respectively, of said reservoir building-blocks wherein each of said populations does not need to be physically separated, in a reservoir or otherwise, from other populations of entities in said complex-systems; and
said linking means allow establishing links between outputs or inputs of any instance of said reservoir building-blocks and inputs or outputs, respectively, of any number of instances of said process building-blocks.

13. A computer-based system as claimed in claim 12 further enabling modeling the dynamic quantitative behavior of said virtual-models or their subsystems, further comprising:
one or more different types of quantitative variables and/or parameters characteristic of the components of said complex-systems associated with said different prototypes of building-blocks and/or their components, and
simulation means, including means associated with each of said types of variables to dynamically compute the values of instances of said variables of building-blocks comprised in a model selected for a simulation run, said values being dependent on the values of one or more instances of variable of other building-block linked to input(s) of said building-blocks.

14. A computer-based system as claimed in claim 10, wherein:
said libraries comprise different prototypes of entity building-blocks, simple or composite, representing different types of entities or entity-components characteristic of said complex-systems, wherein instances of said entity building-blocks are to represent a description of the composition, modular structure, or other characteristics of a representative unit of any of the types of entities that participate in said processes;
said process building-blocks comprise means for any instance to reference the corresponding instance(s) of said entity building-blocks; and
said means further comprise means defined for said process building-blocks to display said referenced instances of entity building-blocks.

15. A computer system as claimed in claim 10 further enabling modeling the dynamic quantitative behavior of said virtual-models or their subsystems, further comprising:
one or more different types of quantitative variables associated with corresponding prototypes of building blocks representing characteristics of the components of said complex-systems they represent; and
method associated with each of said types of variables to dynamically compute the values of any instance of said variables of any instance of corresponding building-block comprised in a model during a simulation run, said values being dependent on the values of any number of variables of other building-blocks linked to input(s) of said instance of building-block.

16. A computer-based system as claimed in claim 1, wherein said libraries comprise one or more prototypes of composite space-compartment building-blocks, which instances are used to represent discrete physical or conceptual space compartments characteristic of said complex-systems, each instance capable of holding any number of instances of said building-blocks, including other instances of space-compartment building-blocks, without any limits as to how many layers of lower-level space-compartment building-blocks are built-in to best partition said complex-system into a hierarchy of subsystems.

17. A computer-based system as claimed in claim 16, wherein:
said libraries comprise one or more different prototypes of process building-blocks comprising one or more inputs and/or outputs, each instance of said prototypes to be used to represent a process of said complex-systems with its input(s) and output(s), different prototypes representing different types of processes characteristic of said complex-systems;
said instances of process building-blocks of said virtual-models are to be organized within instances of space-compartments at the lowest layers of said hierarchy; and
said linking means allow establishing directional links between any of said outputs and inputs of any number of other instances of building-blocks.

18. A computer-based system as claimed in claim 17 further enabling modeling the dynamic quantitative behavior of said virtual-models or their subsystems, further comprising:
one or more different types of variables and parameters embedded in said building blocks, representing characteristics of the components of said complex-systems they represent; and
methods associated with said types of variables to dynamically compute the values of instances of said variables during simulation runs.

19. A computer-based system as claimed in claim 16, wherein:
said libraries comprise one or more prototypes of reservoir building-blocks comprising at least one input or one output, each instance of said prototypes to be used to represent a population of any number of units of entities of one given type, or in one given state or compartment, with its input(s) and/or output(s), and wherein each of said populations does not need to be physically separated, in a reservoir or otherwise, from other populations of entities in said complex-systems; and
said instances of reservoir building-blocks of said virtual-models are to be organized within instances of space-compartments of said hierarchy; and
said linking means allow establishing directional links between any of said outputs and inputs of any number of other instances of building-blocks.

20. A computer-based system as claimed in claim 19 further enabling modeling the dynamic quantitative behavior of said virtual-models or their subsystems, further comprising
one or more different types of quantitative variables associated with corresponding prototypes of building-blocks and/or their components representing characteristics of the components of said complex-systems they represent; and methods associated each of said types of variables to dynamically compute the values of instances of said variables comprised in a model during a simulation run.

21. A method for executing hierarchical virtual-models of any complex-system in a computer-system comprising processor means, memory means, storage means, display means, input means, output means, and program means, comprising the steps of:

loading into said memory means it least one stored persistent data set comprising instances of building-blocks representing the components of said complex-system, wherein:
certain of said prototypes are simple building-blocks;
certain of said types of building-blocks are composite, each instance comprising any number of instances of building-blocks representing its components;
said simple or composite building-blocks;
said building-blocks may comprise any number of attributes with any type of values, including but not limited to: character string, integer or real numbers, logical values, fuzzy values, instances of parameters, variables, lists, arrays, or any other object or data structure, images, or pointers to instances of any of said building-blocks, external files, Uniform Resource Locators (URLs), database records, or any other objects, in said computer system or in a network accessible by said computer system;
executing by said program means for any selected instances of said building-blocks methods providing one or more functions associated with said building-blocks, including show methods defined for composite building-blocks to display the components of the selected instances.

22. A method as claimed in claim 21, wherein said hierarchy of any number of layers include of instances of one or more different types of composite space-compartment building-blocks representing discrete physical or conceptual space compartments of different types or at different levels in a space hierarchy characteristic of said complex-system.

23. A method as claimed in claim 22, wherein the components in said space-compartment hierarchy include any number of instances of one or more different types of process building-blocks with at least one input or one output representing processes characteristic of said complex-systems with their input(s) and/or output(s), and wherein any output of any of said instances is linked to input(s) of any number of other instances of said process building-blocks, further comprising the steps of:

integrating by said program means said linked instances of process building-blocks into a network of multidimensional pathways, wherein any process represented by each node in said network may be comprised in one or more of said pathways, said instances with multiple input links or multiple output links being nodes where different pathways merge or branch, respectively; and
executing by said program means methods to navigate through linked instances of said building-blocks that are downstream and/or upstream of a selected instance in any number of pathways.

24. A method as claimed in claim 23, further enabling dynamic simulations of the quantitative behavior of said virtual-models or their subsystems, wherein quantitative variables and parameters are associated with said instances of building-blocks representing characteristics of the represented components of said complex-systems said program means further comprising simulation means, further comprising the steps of:

requesting a simulation run for any desired combination of one or more interacting pathways, downstream and/or upstream from any one or more selected instances of process building-blocks, and/or for any selected instance(s) of said space-compartment building-blocks;
identifying said program means the set of instances of building-blocks stored in said data set(s) that meet said selected criteria, to be included in said simulation run;
optionally changing the value of any parameters of any of said instances to be included in said simulation run;
controlling the execution of said simulation run; and
dynamically computing by said simulation means the current values over time of said variables for said instances of building-blocks included in said simulation run.

25. A method as claimed in claim 22, wherein the components in said space-compartment hierarchy include any number of instances of one or more different types of reservoir building-blocks with at least one input or one output, each instance representing a population of any number of units of entities of one given type, or in one given state or compartment, with its input(s) and/or output(s), and wherein any output of any of said instances is linked to input(s) of any number of other instances of said reservoir building-blocks, wherein each of said populations of entities does not need to be physically separated in a reservoir or otherwise from other populations of entities in said complex-systems, further comprising the steps of:

integrating by said program means said linked instances of reservoir building-blocks into a network of multidimensional pathways, wherein any reservoir represented by each node in said network may be comprised in one or more of said pathways, said instances with multiple input links or multiple output links being nodes where different pathways merge or branch, respectively; and
executing by said program means methods to navigate through linked instances of said building-blocks that are downstream and/or upstream of any selected instance in any number of pathways.

26. A method as claimed in claim 21, wherein the components in said layers include any number of instances of one or more different types of process building-blocks with at least one input or one output representing processes characteristic of said complex-systems with their input(s) and/or output(s), and wherein any output of any of said instances is linked to input(s) of any number of other instances of said process building-blocks, further comprising the steps of:

integrating by said program means said linked instances of process building-blocks into a network of multidimensional pathways of said interrelated instances, wherein any instance in each node of said network may be comprised in one or more of said pathways, said instances with multiple input links or multiple output links being nodes where different pathways merge or branch, respectively; and
executing by said program means method to navigate through linked instances of said building-blocks that are downstream and/or upstream of a selected instance in any number of pathways.

27. A method as claimed in claim 26, further comprising means for dynamically creating visual displays of said networks of multidimensional pathways representing said complex-systems or their subsystems, further comprising the steps of:

requesting a display of pathways downstream and/or upstream of one or more selected instances of process building-blocks;

identifying by said program means the set of instances of building-blocks stored in said data set(s) that meet said selected criteria, to be represented by the nodes of the network of pathways in said displays;

creating by said program means visual representations of said identified stored instances of process building-blocks; and a dynamically generating a layout on said display means with said visual representations connected as the nodes of a network of one or more pathways, wherein said connectors extended between said visual nodes are directed to indicate a directional relationship.

28. A method-based as claimed in claim 26, wherein:

said instances of process building-blocks are composite and said inputs and outputs are visual components comprising one or more instances of one or more types of reactant building-blocks representing the one or more inputs and the one or more different roles they play in said process, and one or more instances of product building-blocks representing the one or more outputs from said process;

any instance of said product building-blocks of any process building-block is linked to instance(s) of reactant building-blocks of any number of other instances of process building-blocks each instance of reactant building-block being linked to instance(s) of product building-blocks of any number of other instances of process building-blocks; and said instances of process building-blocks are dynamically integrated by said program means into said network of multidimensional pathways based on said links between product and reactant building-block.

29. A method as claimed in claim 26, wherein:

the components in said layers further comprise any number of instances of one or more different types of reservoir building-blocks with at least one input or one output, each instance representing a population of any number of units of entities of one given type, or in one given state or compartment, with its input(s) and/or output(s), wherein each of said populations of entities does not need to be physically separated in a reservoir or otherwise from other populations of entities in said complex-systems;

any output of any of said instances of process building-block is linked to an input of one instance of reservoir building-block and any input of any instance of process building-blocks is linked to an output of one instance of reservoir building-blocks;

said program means integrate said alternating linked instances of reservoir and process building-blocks into said network of multidimensional pathways; and executing by said program means for any of selected instances of reservoir or process building-blocks said one or more methods defined said linked instances of building-blocks may include either one or both of said types of building-blocks, such as said show methods display the linked instance of the complementary building-blocks, or said list methods create lists of said instances of linked reservoir or process building-blocks that are downstream or upstream, in any number of pathways, of a selected instance of reservoir or process building-block.

30. A method as claimed in claim 29, further enabling dynamic simulations of the quantitative behavior of said virtual-models or their subsystems, wherein quantitative variables and parameters are associated with said instances of building-blocks of said virtual models representing characteristics of the represented components of said complex-systems, said program means further comprising simulation means, further comprising the steps of:

requesting a simulation run for any desired combination of one or more interacting pathways, downstream and/or upstream, from any one or more selected instances of reservoir building-blocks, and/or for any selected instance(s) of composite building-blocks of said hierarchy of any number of layers;

identifying by said program means the set of instances of building-blocks stored in said data sets that meet said selected criteria, to be included in said simulation run;

optionally changing the value of any parameters of any of said instances of building-blocks to be included in said simulation run;

using said simulation means for controlling said simulation; and dynamically computing by said simulation means the current values over time of said variables for said instances of building-blocks included in said simulation run.

31. A method as claimed in claim 29, further comprising means for dynamically creating visual displays of said networks of multidimensional pathways representing said complex-systems or their subsystems, further comprising the steps of:

requesting a display of pathways of reservoir and/or process building-blocks downstream and/or upstream of one or more selected instances of reservoir or process building-blocks with a scope comprising one or more selected space-compartment building-blocks;

identifying by said program means the set of instances of building-blocks stored in said data set(s) that meet said selected criteria, to be represented by the nodes of the network of pathways in said displays;

creating by said program means visual representations of said identified stored instances of reservoir and/or process building-blocks; and dynamically generating a layout on said display means with said visual representations connected as the nodes of a network of one or more pathways, wherein said connectors extended between said visual nodes are directed to indicate a directional relationship.

32. A method as claimed in claim 26, wherein said data set(s) further comprise instances of composite entity building-blocks representing descriptions of the composition, modular structure, or other characteristics of a representative unit of any of the types of entities that participate in said processes, which may have references to their corresponding instances of said entity building-blocks, further comprising the steps of:

executing by said program means for any selected instance of said composite entity building-blocks the show methods defined for said building-blocks to display their components representing different types of entity-components characteristic of said entities, without any limits as to how many layers of lower-level composite entity building-blocks are built into any composite entity building-block; and executing by said program means for any selected instances of process building-blocks with said references the show methods defined for said building-blocks to display their corresponding instances of entity building-blocks.

33. A method as claimed in claim 26, further enabling dynamic simulations of the quantitative behavior of said virtual-models or their subsystems, wherein quantitative variables and parameters are associated with said instances of building-blocks representing characteristics of the represented components of said complex-systems, said program means further comprising simulation means, further comprising the steps of:

requesting a simulation run for any desired combination of one or more interacting pathways downstream and/ or upstream from any one or more selected instances of process building-blocks, and/or for any selected instance(s) of composite building-blocks of said hierarchy of any number of layers;

identifying by said program means the set of instances of building-blocks stored in said data set(s) that meet the selected criteria, to be included in said simulation run;

optionally changing the value of any parameters of any of said instances building-blocks to be included in said simulation run;

controlling the execution of said simulation run; and dynamically computing by said simulation means the current values over time of said variables for said instances of building-blocks included in said simulation run.

34. A method as claimed in claim 21, wherein the components in said layers include any number of instances of one or more different types of reservoir building-blocks with at least one input or one output, each instance representing a population of any number of units of entities of one given type, or in one given state or compartment, with its input(s) and/or output(s), and wherein any output of any of said instances is linked to input(s) of any number of other instances of said reservoir building-blocks, wherein each of said populations of entities does not need to be physically separated in a reservoir or otherwise from other populations of entities in said complex-systems, further comprising the steps of:

integrating by said program means said linked instances of reservoir building-blocks into a network of multidimensional pathways, wherein any reservoir represented by each node in said network may be comprised in one or more of said pathways, said instances with multiple input links or multiple output links being nodes where different pathways merge or branch, respectively; and executing by said program means methods to navigate through linked instances of said building-blocks that are downstream and/or upstream of any selected instance in any number of pathways.

35. A method as claimed in claim 34, further enabling dynamic simulations of the quantitative behavior of said virtual-models or their subsystems, wherein variables and parameters are associated with said instances of building-blocks of said virtual models representing characteristics of the represented components of said complex-systems, said program means further comprising simulation means, further comprising the steps of:

requesting a simulation run for any desired combination of one or more interacting pathways, downstream and/ or upstream from any one or more selected instances of reservoir building-blocks, and/or for any selected instance(s) of composite building-blocks of said hierarchy of any number of layers;

identifying by said program means the set of instances of building-blocks stored in said data set(s) that meet said selected criteria, to be included in said simulation run;

optionally changing the value of any parameters of any of said instances of building-blocks to be included in said simulation run;

controlling the execution of said simulation run; and dynamically computing by said simulation means the current values over time of said variables for said instances of building-blocks included in said simulation run.

36. A method as claimed in claim 34, further comprising means for dynamically creating visual displays of networks of connected multidimensional pathways representing said complex-systems or their subsystems, further comprising the steps of:

requesting a display of pathways downstream and/or upstream of one or more selected instances of reservoir building-blocks;

identifying by said program means the set of instances of building-blocks stored in said data set(s) that meet said selected criteria, to be represented by the nodes of the pathways in said displays;

creating by said program means visual representations of said identified stored instances of building-blocks; and dynamically generating a layout on said display means with said visual representations connected as the nodes of a network of one or more pathways, wherein said connectors extended between said visual nodes are directed to indicate a directional relationship.

37. A method as claimed in claim 34, wherein said data set(s) further comprise instances of composite entity building-blocks representing descriptions of the composition, modular structure, or other characteristics of representative units of any of the populations of entities represented by said instances of reservoir building-blocks, which may have references to their corresponding instances of said entity building-blocks, further comprising the steps of:

executing by said program means for any selected instance of said composite entity building-blocks the show methods defined for said building-blocks to display their components representing different types of entity-components characteristic of said entities, without any limits as to how many layers of lower-level composite entity building-blocks are built into any composite entity building-block; and executing by said program means for any selected instances of reservoir building-blocks with said references the show methods defined for said building-blocks to display their corresponding instances of entity building-blocks.

38. A method as claimed in claim 21, wherein said hierarchy of any number of layers include instances of one or more different types of composite time-compartment building-blocks representing discrete physical or conceptual time intervals of different types or at different levels in a time interval hierarchy characteristic of said complex-system.

39. A method as claimed in claim 38, wherein the components in said time-compartments hierarchy include any number of instances of one or more different types of process building-blocks with at least one input or one output representing processes characteristic of said complex-systems with their input(s) and/or output(s), and wherein any output of any of said instances is linked to input(s) of any number of other instances of said process building-blocks, further comprising the steps of:

integrating by said program means said linked instances of process building-blocks into a network of multidimensional pathways, wherein any process represented by each node in said network may be comprised in one or more of said pathways, said instances with multiple input links or multiple output links being nodes where different pathways merge or branch, respectively; and executing by said program means methods to navigate through linked instances of said process building-blocks that are downstream and/or upstream of a selected instance in any number of pathways.

40. A method as claimed in claim 39, further enabling dynamic simulations of the quantitative behavior of said virtual-models or their subsystems, wherein quantitative variables and parameters are associated with said instances of building-blocks representing characteristics of the represented components of said complex-systems, said program means further comprising simulation means, further comprising the steps of:

requesting a simulation run for any desired combination of one or more interacting pathways, downstream and/or upstream from any one or more selected instances of process building-blocks, and/or for any selected instance(s) of said time-compartment building-blocks;

identifying by said program means the set of instances of building-blocks stored in said data set(s) that meet said the selected criteria, to be included in said simulation run;

optionally changing the value of any parameters of any of said instances to be included in said simulation run;

controlling the execution of said simulation run; and dynamically computing by said simulation means the current values over time of said variables for said instances of building-blocks included in said simulation run.

41. A method as claimed in claim 38, wherein the components in said time-compartment hierarchy include any number of instances of one or more different types of reservoir building-blocks with at least one input or one output, each instance representing a population of any number of units of entities of one given type, or in one given state or compartment, with its input(s) and/or output(s), and wherein any output of any of said instances is linked to input(s) of any number of other instances of said reservoir building-blocks, wherein each of said populations of entities does not need to be physically separated in a reservoir or otherwise from other populations of entities in said complex-systems, further comprising the steps of;

integrating by said program means said linked instances of reservoir building-blocks into a network of multidimensional pathways, wherein any reservoir represented by each node in said network may be comprised in one or more of said pathways, said instances with multiple input links or multiple output links being nodes where different pathways merge or branch, respectively; and executing by said program methods to navigate through linked instances of said building-blocks that are downstream and/or upstream of any selected instance in any number of pathways.

42. A computer system for modeling dynamic complex biological systems at different levels of organizational complexity, comprising:

a hierarchy of one or more levels of components representing different levels of biological complexity, any of said levels comprising any number of components including:

components each comprising any number of further levels of components, and linkable components of one or more different types representing interrelated components characteristic of the corresponding level of complexity of said biological systems, including one or more different types of components representing various types of biological processes; and program means for creating and/or manipulating executable models of said complex biological systems based on said one or more levels and their linkable components.

43. A computer system as claimed in claim 42, wherein any of said linkable components is linked to any number of other linkable components in the same level or in different levels.

44. A computer system as claimed in claim 42, wherein said linkable components further comprise any number of interrelated variables characteristic of the biological components they represent for modeling the dynamic behaviour of said complex biological system.

45. A computer system as claimed in claim 42, wherein said linkable components further include one or more different types of components representing various populations of entities that participate in said biological processes as inputs and/or outputs, each of said populations comprising biological or chemical entities of any one given type, or any one given state or compartment, characteristic of the corresponding level of complexity.

46. A computer system as claimed in claim 42, wherein any of said linkable components representing one of said populations of entities is linked to any number of said linkable components representing biological processes which provide inputs to or receive outputs from said population.

47. A computer system as claimed in claim 42, wherein said program means include means for navigating through the information provided by said one or more levels and their linkable components.

48. A computer system as claimed in claim 42, wherein said program means include means for synthesizing and presenting to users new information from the information provided in said one or more levels of linkable components.

* * * * *